(12) United States Patent
Nilles et al.

(10) Patent No.: US 7,344,718 B2
(45) Date of Patent: Mar. 18, 2008

(54) YERSINIA SPECIES COMPOSITIONS

(75) Inventors: Matthew L. Nilles, Grand Forks, ND (US); Jyl S. Matson, Ann Arbor, MI (US)

(73) Assignee: University of North Dakota, Grand Forks, ND (US)

( * ) Notice: Subject to any disclaimer, the term of this patent is extended or adjusted under 35 U.S.C. 154(b) by 447 days.

(21) Appl. No.: 10/622,220

(22) Filed: Jul. 18, 2003

(65) Prior Publication Data

US 2004/0151727 A1 Aug. 5, 2004

Related U.S. Application Data

(60) Provisional application No. 60/444,076, filed on Jan. 31, 2003.

(51) Int. Cl.
*A61K 39/00* (2006.01)
*C07K 1/00* (2006.01)

(52) U.S. Cl. .................... 424/184.1; 530/350
(58) Field of Classification Search ............. 424/184.1; 530/350
See application file for complete search history.

(56) References Cited

U.S. PATENT DOCUMENTS 5,985,285 A 11/1999 Titball et al.
6,261,561 B1 * 7/2001 Stewart et al. ............ 424/184.1

FOREIGN PATENT DOCUMENTS

| WO | WO 95/18231 | 7/1995 |
|----|-------------|--------|
| WO | WO 96/28551 | 9/1996 |
| WO | WO 98/24912 | 6/1998 |
| WO | WO 02/077249 | 10/2002 |

OTHER PUBLICATIONS

Plotkin et al (VACCINES W B Saunders Co. 1988, p. 571).*
8th International Symposium on Yersinia, Sep. 4-8, 2002. Turku, Finland.
Benner et al., Immune Response to Yersinia Outer Proteins and Other Yersinia pestis Antigens after Experimental Plague Infection in Mice, Infection and Immunity, Apr. 1999, pp. 1922-1928, vol. 67, No. 4.
Edqvist et al., YscP and YscU Regulate Substrate Specificity of the Yersinia Type III Secretion System, Journal of Bacteriology, Apr. 2003, pp. 2259-2266, vol. 185, No. 7.
Hoiczyk et al., Polymerization of a single protein of the pathogen Yersinia entercolitica into needles punctures eukaryotic cells, PNAS, Apr. 10, 2001, pp. 4669-4674, vol. 98, No. 8.
Titball et al., Vaccination against bubonic and pneumonic plague, Vaccine, 2001, pp. 4175-4184, vol. 19.
Williamson, E.D., Plague vaccine research and development, Journal of Applied Microbiology, 2001, pp. 606-608, vol. 91.
Wilson et al., Role of EscF, a putative needle complex protein, in the type III protein translocation system of enteropathogenic *Escherichia coli*, Cellular Microbiology, 2001, pp. 753-762, vol. 3, No. 11.
Michiels et al., Analysis of virC, an Operon Involved in the Secretion of Yop Proteins by Yersinia enterocolitica, Journal of Bacteriology, Aug. 1991, pp. 4994-5009, vol. 173, No. 16.
Hu et al., Structural Organization of Virulence-Associated Plasmids of Yersinia pestis, Journal of Bacteriology, Oct. 1998, pp. 5192-5202, vol. 180, No. 19.
Supplementary Partial European Search Report, EP 04 74 9309, dated Mar. 29, 2007.

* cited by examiner

*Primary Examiner*—Mark Navarro
(74) *Attorney, Agent, or Firm*—TraskBritt

(57) ABSTRACT

A method of protecting an animal from infections with pathogens originating from *Yersinia* comprising administering an isolated or recombinant YscF protein to the animal is disclosed. The isolated or recombinant YscF protein may be administered as a vaccine. An isolated or recombinant YscF protein capable of conferring protection to an animal against a pathogen of a *Yersinia* origin is further disclosed. Nucleic acid molecules encoding the isolated or recombinant YscF protein are also disclosed. In other embodiments, antibodies generated against the isolated or recombinant YscF protein capable of conferring protection to an animal against a pathogen or a *Yersinia* origin and uses of the antibodies are described.

6 Claims, 5 Drawing Sheets

FIG. 1

```
                          1                                                    50
       Ht-YscF         (1) MSNFSGFTKGTDIADLDAVAQTLKKPADDANKAVNDSIAALKDKPDNPAL  (SEQ ID NO:12)
YscF - Y pestis KIM5   (1) MSNFSGFTKGTDIADLDAVAQTLKKPADDANKAVNDSIAALKDKPDNPAL  (SEQ ID NO:17)
YscF - Y. pestis CO92  (1) MSNFSGFTKGTDIADLDAVAQTLKKPADDANKAVNDSIAALKDKPDNPAI  (SEQ ID NO:18)
YscF - Y. enterocolitica (1) MSNFSGFAKGTDIITDLDAVAQTLKKPADDANKAVNDSIAALKDKPDNPAI  (SEQ ID NO:4)
           Consensus   (1) MSNFSGFTKGTDIADLDAVAQTLKKPADDANKAVNDSIAALKDTPDNPAL 51                                              95
       Ht-YscF        (51) LADLQHSINKWSVIYNINSTIVRSMKDLMQGILQKFPLEHHHHHH      (SEQ ID NO:12)
YscF - Y pestis KIM5  (51) LADLQHSINKWSVIYNINSTIVRSMKDLMQGILQKFP              (SEQ ID NO:17)
YscF - Y. pestis CO92 (51) LADLQHSINKWSVFYNINSTIVRSMKDLMQGILQKFP              (SEQ ID NO:18)
YscF - Y. enterocolitica(51) LADLQHSINKWSVIYNMSSTIVRSMKDLMQGILQKFP            (SEQ ID NO:4)
           Consensus  (51) LADLQHSINKWSVIYNINSTIVRSMKDLMQGILQKFP              (SEQ ID NO:19)
```

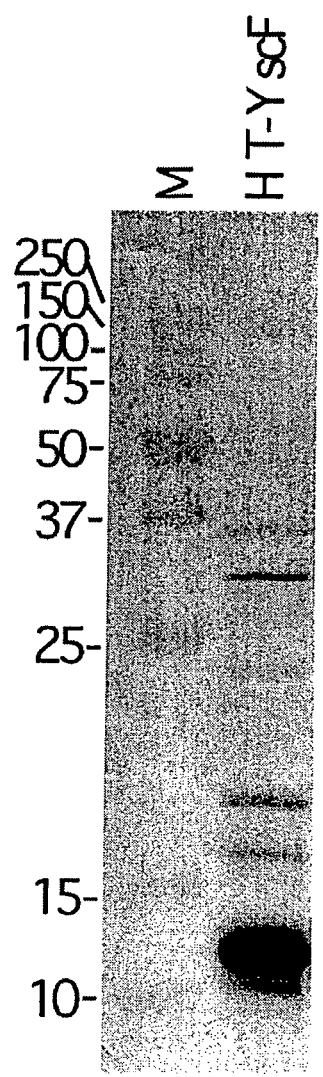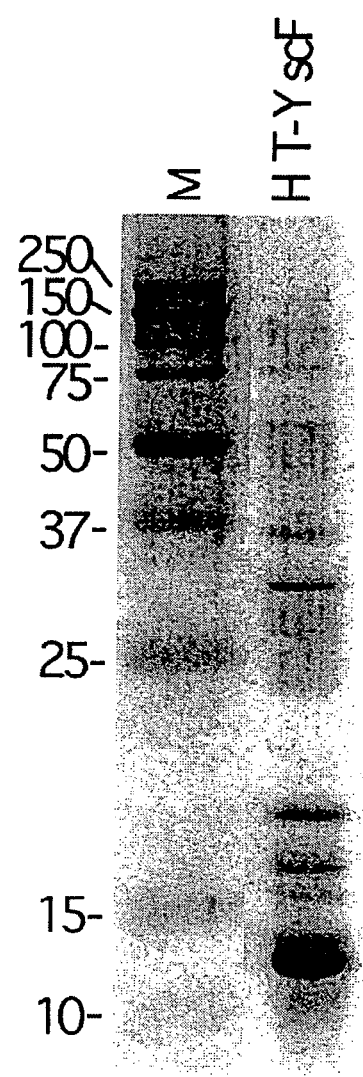
Penta-His Antibody
GelCode Blue Stain
*FIG. 4A*
*FIG. 4B*

YERSINIA SPECIES COMPOSITIONS

CROSS-REFERENCE TO RELATED APPLICATIONS

Pursuant to 35 U.S.C. § 119(e), this application claims the benefit of U.S. Provisional Application 60/444,076, filed Jan. 31, 2003.

TECHNICAL FIELD

The invention relates generally to the field of biotechnology, and more particularly to compositions for eliciting an immune response including an isolated or recombinant YscF or an epitope thereof that provides protection against infections caused by members of the genus *Yersinia*.

BACKGROUND

*Yersinia pestis* causes a rapidly progressing disease in humans with a high mortality rate. Due to the severe nature of the disease and its ability for aerosol transmission, a better vaccine for the disease caused by *Y. pestis*, the plague, is desirable. Current efforts for vaccine development have focused on two proteins: LcrV and the F1 antigen (25). The best results to date have been obtained by using a combination of recombinant LcrV and F1 subunits (25). This vaccine demonstrates protection against both pneumonic and systemic forms of plague (25). One of the potential limitations of this vaccine is that the F1 antigen is not required for full virulence of *Y. pestis* as F1-negative strains have the same $LD_{50}$ value as F1-positive strains (6-8, 27). While the recombinant sub-unit vaccine is effective and offers protection against F1 minus strains of *Y. pestis*, the inclusion of other antigens with the LcrV-F1 vaccine could improve the ability of the resulting vaccine to offer protection against multiple *Y. pestis* strains, or new antigens could be developed as separate vaccine candidates. Another *Yersinia* protein that has been shown to provide some protection is YopD (25).

The type III secretion apparatus is encoded on the low-calcium response (LCR) virulence plasmid, pCD1 in strain KIM (20) of *Y. pestis*. The type III secretion apparatus is a conserved virulence mechanism that is absolutely required for virulence of *Y. pestis* (19). YscF (See, SEQ ID NOS: 1 and 2 for the amino acid sequence and the yscF sequence, respectively) is a surface localized protein that is required both to secrete Yops and to translocate toxins into eukaryotic cells (1, 10, 12). The type III secretion apparatus and YscF are also encoded for by the virulence plasmids of *Yersinia pseudotuberculosis* and *Yersinia enterocolitica*. *Y. pseudotuberculosis* and *Y. enterocolitica* are enteropathogenic bacteria transmitted by the oral route and cause a range of gastrointestinal diseases collectively referred to as yersiniosis. The nucleic acid sequence for YscF of *Y. pseudotuberculosis* and the amino acid sequence for YscF of *Y. pseudotuberculosis* are substantially similar to the yscF gene and YscF protein of *Y. pestis* based on homologies and comparisons of other proteins of the type III secretion complex. The nucleic acid sequence encoding YscF of *Y. enterocolitica* includes SEQ ID NO: 3 and the amino acid sequence contains SEQ ID NO: 4. An alignment of the YscF proteins from these organisms is illustrated in FIG. 1.

One report speculates that YscF polymerization is required for a YscF needle to puncture eukaryotic cell membranes (12). Other researchers suggest that YscF and its homologs function to provide a base that a translocon complex is built upon, or that YscF builds a conduit from the bacterium to the eukaryotic membrane (4). This suggestion seems more likely given that other proteins such as YopB, YopD, and LcrV are also required for translocation into eukaryotic cells (9, 11, 13, 17, 18, 21, 23, 24). However, the exact function of YscF remains unknown.

Other pathogenesis-related type III secretion systems possess homologs to YscF. In pathogenic *Salmonella* and *Shigella*, the YscF homologs (PrgI (See, SEQ ID NOS: 5 and 6 for the amino acid sequence and nucleic acid sequences, respectively) and MxiH, respectively, (See, SEQ ID NOS: 7 and 8 for the amino acid sequence and nucleic acid sequence, respectively)) have been demonstrated to form a needle structure that protrudes from the surface of bacterial cells (2, 15, 16). The best characterized homolog of YscF is EscF (See, SEQ ID NOS: 9 and 10 for the amino acid sequence and nucleic acid sequence, respectively) of enteropathogenic *E. coli* (EPEC). EscF is required for "attaching and effacing" (A/E) lesion formation on the intestinal mucosa and for type III secretion of effector proteins (5, 22, 29). EscF is thought to be a structural component of the needle complex on the bacterial surface as it binds EspA, the major component of a filamentous surface organelle, and is required for formation of the EspA filaments (5, 22, 29). However, this surface localization has never been directly visualized and the only EscF antiserum generated was unable to recognize the native protein (29).

Based on the fact that YscF is thought to be a surface-expressed protein in the pathogens of *Yersinia* and is required for virulence, it was determined whether YscF could serve as a protective antigen against experimental infection with pathogens of *Yersinia*.

SUMMARY OF THE INVENTION

In one exemplary embodiment, a composition of matter comprising YscF of a *Yersinia* origin is disclosed. The composition of matter may comprise isolated or recombinant YscF; a recombinant vector including the nucleic acid associated with isolated or recombinant YscF; synthetic YscF; a nucleic acid encoding the isolated or recombinant YscF; a recombinant nucleic acid which comprises a nucleotide sequence originating from the genome of *Yersinia*; a polypeptide having an amino acid sequence originating from a protein of *Yersinia*, the polypeptide being produced by a cell capable of producing it due to genetic engineering with appropriate recombinant DNA; an isolated or synthetic antibody which specifically recognizes a part or epitope of the isolated or recombinant YscF; or a recombinant vector which contains nucleic acid comprising a nucleotide sequence coding for a protein or antigenic peptide associated with isolated or recombinant YscF.

In another exemplary embodiment, a recombinant nucleic acid, more specifically recombinant DNA, which comprises a nucleotide sequence encoding for isolated or recombinant YscF, as shown in SEQ ID NO: 11 is disclosed (see, SEQ ID NO: 12 for the amino acid sequence encoded by SEQ ID NO: 11). In a further embodiment, a pharmaceutical composition including the nucleotide sequence encoding for isolated or recombinant YscF is disclosed. Use of the recombinant nucleic acid encoding the isolated or recombinant YscF for the prophylaxis of an animal is also disclosed.

In an additional embodiment, a peptide comprising an isolated or recombinant YscF amino acid sequence is disclosed. The YscF proteins disclosed herein are capable of conferring protection to an animal against a pathogen or *Yersinia* origin. In a further embodiment, a pharmaceutical composition including the isolated of recombinant YscF is disclosed. Use of the isolated or recombinant YscF for the prophylaxis of an animal is also disclosed.

In yet another embodiment, a vaccine for vaccinating animals, in particular mammals, to protect them against infections caused by pathogens of *Yersinia* origin, such as *Y. pestis, Y. pseudotuberculosis* and *Y. enterocolitica* is disclosed. The vaccine comprises isolated or recombinant YscF; a recombinant vector which contains the nucleic acid coding for a protein or antigenic peptide associated with isolated or recombinant YscF; an antigenic part or epitope of isolated or recombinant YscF; or a peptide mimicking an antigenic component of isolated or recombinant YscF; together with a suitable carrier or adjuvant.

Use of a composition comprising an isolated or recombinant YscF for the manufacture of a medicament for the treatment of a mammal infected with a *Yersinia* pathogen, such as *Y. pestis, Y. pseudotuberculosis* or *Y. enterocolitica* is further disclosed. In a further aspect, the invention discloses the use of a composition comprising antibodies or fragments thereof that bind to isolated or recombinant YscF for the manufacture of a medicament for the treatment of a mammal infected with a *Yersinia* pathogen, such as *Y. pestis, Y. pseudotuberculosis* or *Y. enterocolitica* or prevention of such an infection.

In a further exemplary embodiment, a diagnostic kit for detecting antibodies generated against isolated or recombinant YscF in a sample, in particular a biological sample such as blood or blood serum, sputum, saliva, or tissue (i.e., lymph nodes), originating from an animal, in particular a mammal is disclosed. The diagnostic kit comprises an antibody or fragment thereof that binds to the isolated or recombinant YscF or a fragment thereof, and suitable detection means of an antibody detection assay.

The invention also discloses a diagnostic kit for detecting an antigen or epitope originating from YscF in a sample, in particular a biological sample such as blood or blood serum, sputum, saliva, or tissue, derived from an animal, in particular a mammal, comprising an antibody or fragment thereof that recognizes a part or epitope of YscF, and suitable detection means of an antigen detection assay.

In a further embodiment, a process for diagnosing whether an animal, in particular a mammal, is carrying the antibodies directed against isolated or recombinant YscF is disclosed. The process comprises preparing a sample, in particular a biological sample such as blood or blood serum, sputum, saliva, or tissue, derived from the animal, and examining whether the biological sample contains the isolated or recombinant YscF antigen, or an antibody specifically recognizing the isolated or recombinant YscF, the YscF being associated with infections caused by bacteria of the *Yersinia* species.

A method for vaccinating a mammal comprising cloning a nucleic acid sequence encoding an isolated or recombinant YscF of a *Yersinia* origin or a homolog thereof into an expression vector is disclosed in another embodiment. The method further includes inducing the expression of the nucleic acid and collecting the isolated or recombinant YscF or homologs thereof. The isolated or recombinant YscF or homolog thereof is administered to an animal, such as a mammal, to generate an immune response against the isolated or recombinant YscF or homolog thereof.

A process for manufacturing a composition for use in vaccinating animals is also disclosed. The process comprises cloning a nucleic acid sequence encoding an isolated or recombinant YscF or homolog thereof into an expression vector. The process further includes inducing the expression of the nucleic acid and collecting the isolated or recombinant YscF. The isolated or recombinant YscF or homolog thereof is mixed with a pharmaceutically acceptable excipient to produce the composition.

In an additional embodiment, a method for generating an immune response is disclosed. The method includes cloning a nucleic acid sequence encoding an isolated or recombinant YscF or a homolog thereof into an expression vector. The method further includes inducing the expression of the nucleic acid and collecting the isolated or recombinant YscF or homolog thereof. The isolated or recombinant YscF or homolog thereof is administered to a subject to generate the immune response in the subject.

A method of collecting antibodies generated against an epitope of an isolated or recombinant YscF or homolog thereof is disclosed in a further embodiment. The method includes cloning a nucleic acid sequence encoding the isolated or recombinant YscF or a homolog thereof into an expression vector. The method further includes inducing the expression of the nucleic acid and collecting the isolated or recombinant YscF or homolog thereof. The isolated or recombinant YscF or a homolog thereof is administered to a subject. The isolated or recombinant YscF or a homolog thereof is immobilized on a substrate and serum collected from the subject is added to the substrate such that antibodies in the serum directed against the isolated or recombinant YscF or a homolog thereof adhere to the immobilized protein.

In an additional embodiment, a peptide corresponding to an epitope of the isolated or recombinant YscF or homolog thereof to which an antibody binds is disclosed. A composition or vaccine including the epitope of the isolated or recombinant YscF or homolog thereof to which an antibody binds is further disclosed. The use of a composition comprising the epitope of the isolated or recombinant YscF or homolog thereof to which an antibody binds for the manufacture of a medicament for the treatment of a mammal infected with a pathogen of *Yersinia* origin, such as such as *Y. pestis, Y. pseudotuberculosis* or *Y. enterocolitica* is further disclosed.

BRIEF DESCRIPTION OF THE DRAWINGS

FIG. 1 is a sequence alignment of peptide sequences of the YscF protein from various *Yersinia* bacteria including SEQ ID NOS: 4, 13, 17, 18 and 19.

FIGS. 4A and 4B illustrate recovered His-tagged YscF protein run on a SDS-PAGE.

BEST MODE OF THE INVENTION

Figure 2:
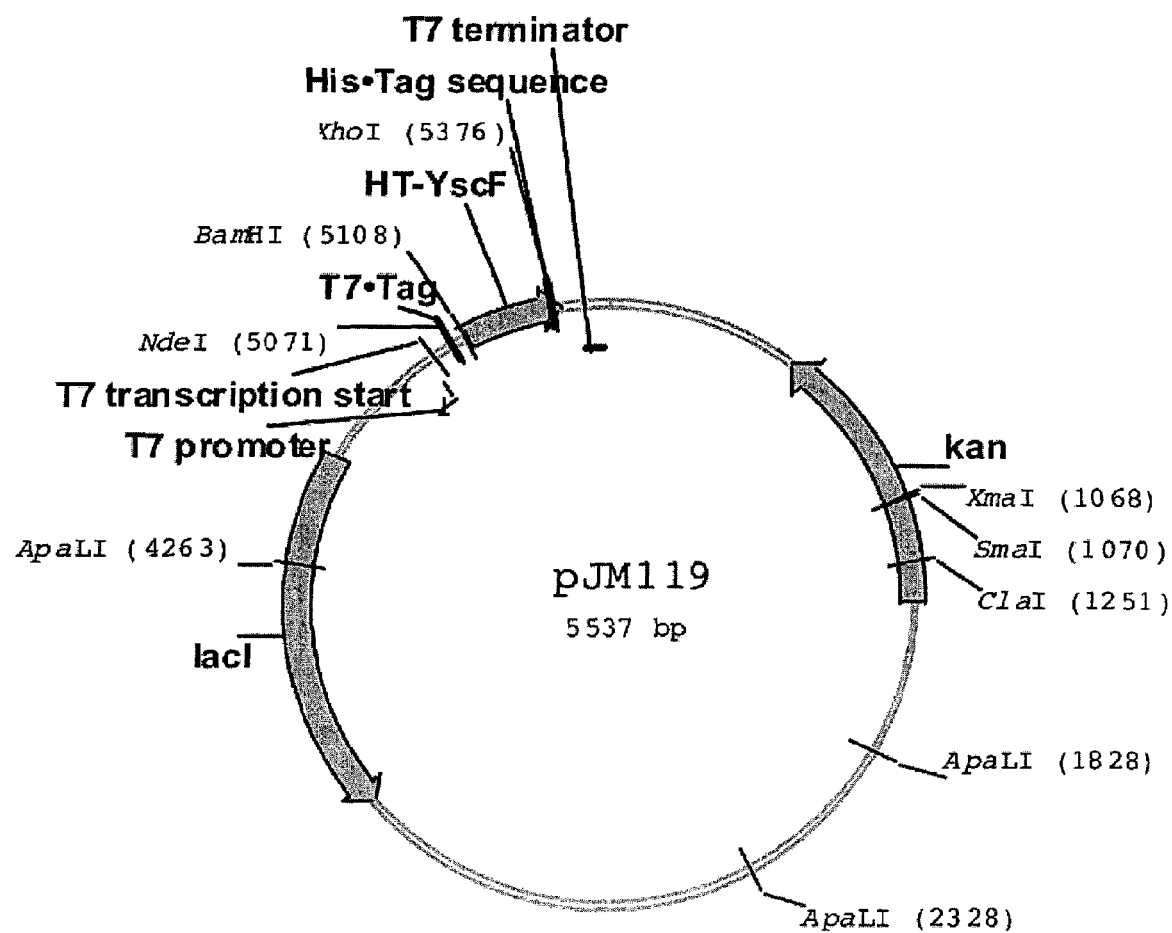
FIG. 2 is a map of the pJM119 plasmid (SEQ ID NO: 13).

The embodiments described herein disclose the successful immunization of mice with isolated or recombinant YscF. Previous attempts to immunize mice against subsequent challenge with *Y. pestis* have failed. For instance, Hill et al. immunized mice with YscF, but were not able to show protection in the mice against subsequent challenge with *Y. pestis*. (See, Hill et al., *Immunological characterization of sub-units of the Yersinia type III secretion apparatus*, Abstract at the 8th International Symposium on *Yersinia*. Sep. 4-8, 2002. Turku, Finland.). Thus, the present invention discloses a surprising discovery that isolated or recombinant YscF is able to protect subjects against subsequent challenge with a pathogen of *Yersinia* origin. The immunization disclosed herein results in a high anti-YscF titer and protection against challenge with a pathogen of *Yersinia* origin. The embodiments described herein disclose that YscF provides protection against challenge with a pathogen of *Yersinia* origin and, thus, is a vaccine candidate. The isolated or recombinant YscF may also be used in conjunction with the other known plague antigens.

The phrase "suitable excipient" as used herein means that an active ingredient can be formulated, for example, with the conventional generally non-toxic, well-known pharmaceutically acceptable carriers (e.g., sterile water, saline solution and other acceptable carriers) for making suitable pharmaceutical compositions. The suitable excipient may also include adjuvants as described herein. A person of ordinary skill in the art will recognize that a suitable excipient, examples of which are provided herein, is an art recognized term.

The vaccine may also comprise compounds including an adjuvant activity. Adjuvants are non-specific stimulators of the immune system and enhance the immune response of the animal host to the vaccine. Examples of adjuvants that may be used include, but are not limited to, incomplete Freund's adjuvant, Freunds Complete adjuvant, vitamin E, non-ionic block polymers, muramyldipeptides, ISCOMs (immune stimulating complexes), Saponins, mineral oil, vegetable oil, Carbopol, Alhydrogel, and Ribi. Adjuvants suitable for mucosal application include *E. coli* heat-labile toxin or *Cholera* toxin. Other suitable adjuvants include aluminum hydroxide, aluminum phosphate or aluminum oxide, oil-emulsions or vitamin-E solubilisate. The vaccine may also include preservatives to increase the shelf live of the vaccine.

In the exemplary embodiments herein, the vaccines or compositions including the isolated or recombinant YscF of *Yersinia* origin or homologs thereof may also include pharmaceutically acceptable carriers including, but not limited to, water, culture fluid in which the bacteria were cultured, a solution of physiological salt concentration, stabilizers such as SPGA, carbohydrates (e.g., sorbitol, mannitol, starch, sucrose, glucose, dextran), proteins such as albumin or casein, protein containing agents such as bovine serum or skimmed milk, and buffers (e.g., phosphate buffer). When stabilizers are added to the vaccine, the vaccine is suitable for freeze-drying. Accordingly, in another exemplary embodiment, the vaccine may be in a freeze-dried form as is known by those of ordinary skill in the art.

The vaccines of the exemplary embodiments may be administered to humans or animals inter alia intraperitoneally, intranasally, intradermally, subcutaneously, orally, by aerosol or intramuscularly. As known in the art, the vaccine may be in a unit dosage form and provided in sterile form in a sealed container. The dosage administered to the animal will vary depending on the age, weight and animal vaccinated, as well as the mode of administration and the frequency of administrations employed. Regimens for inducing an immune response including dose and therapy may be guided by the initial response of the animal to the first vaccine dose and clinical judgment as known by those of ordinary skill in the art.

Types of animals that the vaccine may be administered to include any mammal, such as humans, pigs, mice, prairie dogs, cats, dogs and rats or other animals. The vaccine may be used to generate a "herd immunity" in a population or a sub-population of animals. As known in the art, the phrase "herd immunity" refers to the effect achieved when enough individuals of the population or sub-population are vaccinated such that the particular disease is not able to spread through the population or sub-population. Thus, the immunized individuals are protected as are the non-immunized individuals since the disease cannot effectively spread through the population or sub-population. Accordingly, the vaccine has utility in a public health program designed to help prevent the transmission of infections caused by pathogens of *Yersinia* origin.

The phrase "pathogens of *Yersinia* origin" will be used to refer to members of the genus *Yersinia* that cause disease including, but not limited to, *Y. pestis, Y. pseudotuberculosis* and *Y. enterocolitica* which encode substantially identical and functionally equivalent YscF proteins. As described herein, the term "YscF" will be used to refer to the YscF protein originating from any of *Y. pestis, Y. pseudotuberculosis, Y. enterocolitica* unless otherwise specified. The YscF proteins of *Y. pestis* and *Y. enterocolitica* include substantially similar sequences as indicated in the alignment of FIG. 1. Further, since many proteins of the type III secretion complex of both *Y. pestis* and *Y. pseudotuberculosis* are substantially similar, YscF from *Y. pestis* and *Y. pseudotuberculosis* are considered to be substantially similar.

The term "protective" or "conferring protection" as used herein with reference to a protein will be used to refer to the ability of the protein to increase the lethal dose of pathogenic bacteria required to kill 50% of hosts infected with the pathogenic bacteria after administration of the protein to the host.

As used herein, the term "recombinant YscF" will be used to refer to a YscF protein that includes amino acid residues in addition to or different than wild-type YscF. For instance, His-tagged YscF is a recombinant YscF (see, SEQ ID NOS: 11 and 12 for the nucleic acid and amino acid sequences of His-tagged YscF, respectively).

In addition to the peptides, vaccines and compositions including isolated or recombinant YscF or homologs thereof described herein, peptides functionally and immunologically related to the isolated or recombinant YscF or homologs thereof that possess the same functions and immunologic properties as the isolated or recombinant YscF or analogs thereof are further disclosed. For instance, amino acid substitutions in the peptide may not substantially alter the biological and immunological activities of the protein and have been described, e.g., Neurath et al. in "The Proteins" Academic Press, New York (1979). Amino acid replacements which occur frequently in evolution and do not alter the function or immunological activity of the protein include inter alia, Ser/Ala, Ser/Gly, Asp/Gly, Asp/Asn, Ile/Val (see, Dayhof. M. C., Atlas of protein sequence and structure, Nat. Biomed, Res. Found., Washington D.C., 1978, vol. 5, suppl. 3). Other amino acid substitutions that often do not alter the function of immunogenicity of proteins include Asp/Glu, Thr/Ser, Ala/Gly, Ala/Thr, Ser/Asn/Ala/Val, Thr/Phe, Ala/Pro, Lys/Arg, Leu/Ile, Leu/Val and Ala/Glu. Based on this information, Lipman and Pearson have developed a method for rapid and sensitive protein comparison (*Science,* 227, 1435-1441, 1985) and determining the functional similarity between homologous proteins. Accordingly, amino acid substitutions which do not alter the function or immunological properties of the isolated or recombinant YscF or homologs thereof, are encompassed by the present invention.

In addition to the nucleotide sequences, vaccines or compositions including the nucleotide sequences encoding for the isolated or recombinant YscF or homologs thereof, nucleotide sequences having substantially similar functions as the nucleotides encoding the isolated or recombinant YscF or homologs thereof are further disclosed. For instance, as known in the art, the degeneracy of the genetic code and the "wobble" hypothesis allows for nucleotide substitutions to occur and, yet, the altered nucleotide sequence encodes a protein having a substantially similar function or immunogenicity as the proteins encoded by original nucleotide sequence since some amino acids are encoded by more than one codon.

Further, as previously described herein, some amino acid substitutions may not alter the function or immunological properties of the protein. For instance, single nucleotide polymorphisms, allelic variants, insertions and deletions may have different nucleotide sequences from those disclosed herein, but still encode isolated or recombinant YscF proteins or homologs thereof. Accordingly, nucleotide substitutions in the nucleic acids of the present invention which do not substantially alter the peptide sequence of the isolated or recombinant YscF proteins or homologs thereof and nucleotide substitutions which encode for proteins having substantially the same function or immunological properties as the isolated or recombinant YscF proteins or homologs thereof are encompassed by the present invention. Thus, nucleic acid sequences that hybridize to the nucleic acid sequences encoding the isolated or recombinant YscF or homologs thereof under highly stringent conditions, such as high salt conditions, are within the scope of the present invention.

EXAMPLE I

Expression and Purification of HT-YscF

Figure 3:
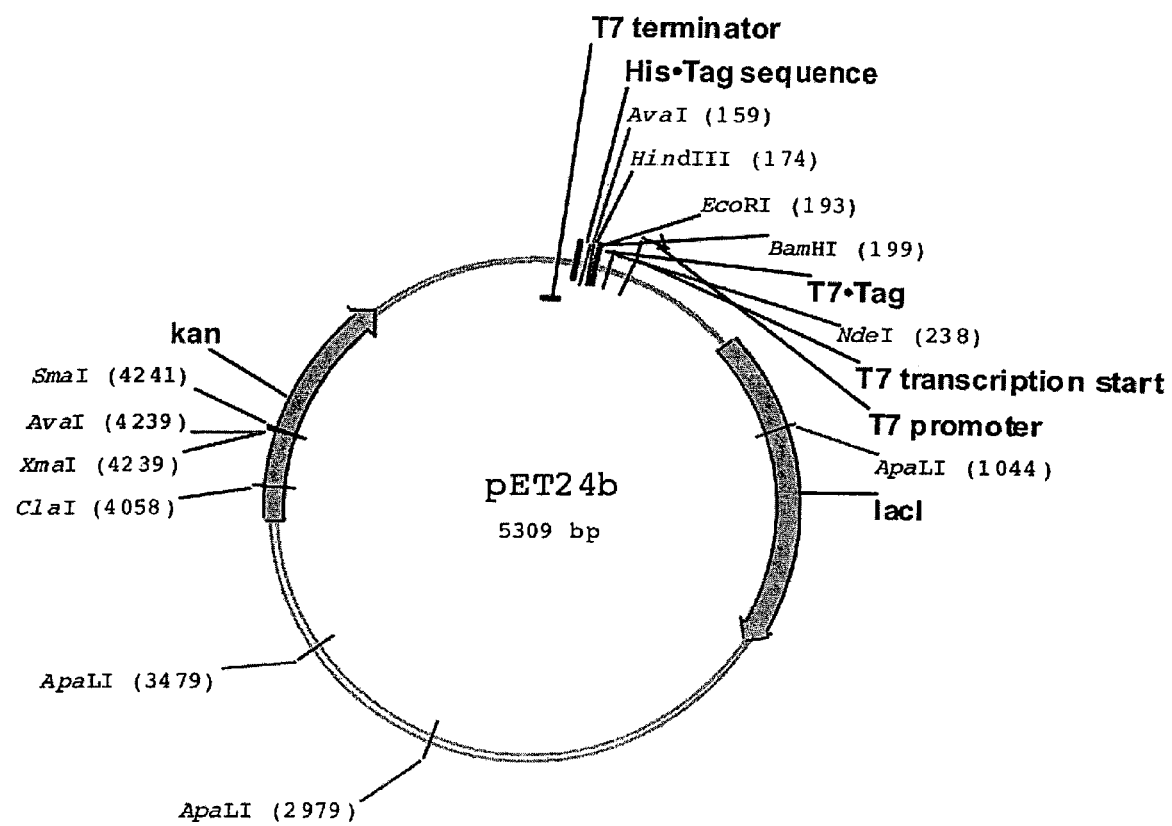
FIG. 3 is a map of the pET24b plasmid (SEQ ID NO: 14).

Expression and purification of HT-YscF. Plasmid pJM119 (See, FIG. 2 and SEQ ID NO: 13) was constructed by cloning a BamHI- and XhoI-cleaved PCR product into pET24b (SEQ ID NO: 14), a cloning vector commercially available from Novagen of Madison, Wis. (See, FIG. 3). The primers used to amplify yscF were HT-YscF Start (5' CGG GAT CCG ATG AGT AAC TTC TCT GGA TTT 3') (SEQ ID NO: 15) and HT-YscF Stop (5' CCG CTC GAG TGG GAA CTT CTG TAG GAT GCC 3') (SEQ ID NO: 16). *E. coli* BL21(DE3) (commercially available from Novagen of Madison, Wis.) harboring pJM119 was grown in one liter of LB broth containing carbenicillin at 37° C. Expression of HT-YscF was induced after 2 h of growth with 0.3 mM IPTG and incubated until the $A_{550}$ reached ~1.0.

Cells were harvested by centrifugation and disintegrated by passage through a French pressure cell at 20,000 lb/in². Subsequent to disintegration, the extracts were clarified by centrifugation at 3200×g for 20 min at 4° C. Affinity purification of His-tagged YscF (HT-YscF) was performed using Talon resin (Clontech of Palo Alto, Calif.) as described by the manufacturer. Purity of the recovered protein was estimated by SDS-PAGE on a 15% (wt/vol) gel followed by staining with Gelcode Blue (Pierce of Rockford, Ill.). The purified protein ran as multiple bands on the gel. A band that corresponded to the predicted size of HT-YscF was the dominant species and other larger bands could also be visualized (See, FIGS. 4A and 4B). Based on the sizes of the larger bands and the fact that they are recognized by the penta-His antibodies, it is likely that the larger bands represent dimers and other multimers of YscF. This is not surprising as YscF and its homologs are known to form multimeric structures.

EXAMPLE II

The His-tag is removed from the isolated His-tagged YscF protein using known processes. For instance, treatment of the His-tagged YscF protein with Staphlylococcal peptidase I, (Protease V8) which is commercially available from Worthington Biochem of Lakewood, N.J. is performed. (See, Birktoft J. J., et al., *Glutamyl endopeptidases*, Methods of Enzymology (1994) 244: 114126). Cleavage of the His-tagged YscF with Staphlylococcal peptidase I results in breaking of the peptide bond between amino acid 89 and 90 of the His-tagged YscF (SEQ ID NO: 12), and results in the YscF (SEQ ID NO: 1) with an additional two amino acids, leucine and glutamate, on the carboxyl terminus. Staphylococcal peptidase I is also referred to as glutamyl endopeptidase.

EXAMPLE III

In other exemplary embodiments, the nucleic acid sequences encoding YscF from *Y. enterocolitica* (SEQ ID NO: 3) or *Y. pseudotuberculosis* or the homologs of YscF, i.e., the nucleic acids encoding PrgI, MxiH and EscF (SEQ ID NOS: 6, 8 and 10), respectively, are cloned and expressed. In this manner, His-tagged YscF from *Y. enterocolitica* or *Y. pseudotuberculosis* or His-tagged PrgI, MxiH and EscF proteins are collected and mixed with a suitable excipient to form a pharmaceutical composition. The pharmaceutical composition is used to immunize mice.

EXAMPLE IV

Immunization Protocol

Active immunization of outbred mice followed by challenge with *Y. pestis* KIM5. KIM5 is a strain of *Y. pestis* that when administered to a mammal, causes an infection in substantially the same manner as wild-type *Y. pestis*. For challenge with *Y. pestis*, 6- to 8-week-old female Swiss-Webster mice were immunized i.p. (intraperitoneally) with 40 μg/mouse His-tagged YscF or phosphate-buffered saline (3) PBS (control mice) emulsified 1:1 with complete Freund's adjuvant (CFA). Experimental mice were boosted with 40 μg/mouse His-tagged YscF in incomplete Freund's adjuvant (IFA) at two weeks and 20 μg/mouse His-tagged YscF in IFA at 4 weeks post-immunization. Negative control mice received PBS emulsified with IFA. Two weeks after the final immunization, groups of 10 mice were challenged i.v. (intravenously) via the retro-orbital sinus with $10^1$ to $10^6$ CFU (colony forming units) *Y. pestis* KIM5 in PBS. The mice were observed for 19 days after challenge, and the average doses required to kill 50% of the mice ($LD_{50}$) for the treatment groups were calculated using the extrapolation method of Reed and Muench (26).

EXAMPLE V

The vaccine including the isolated or recombinant YscF is combined with other antigens protective against infections with bacteria, such as *Yersinia* bacteria, including LcrV, F1 antigen, YopD and a live attenuated *Yersinia* bacterium (EV76 strain), a live recombinant carrier bacterium including a nucleic acid encoding the isolated or recombinant YscF, an inactive or killed whole cell *Yersinia* bacterium and any combinations thereof In a further embodiment, the vaccine including the isolated or recombinant YscF is combined with homologs of YscF including PrgI, MxiH, EscF and mixtures thereof.

EXAMPLE VI

In another exemplary embodiment, the nucleic acids encoding the isolated or recombinant YscF of *Yersinia* origin or homologs thereof are introduced into an animal through a microorganism (e.g. a bacterium or a virus) in such a way that the recombinant microorganism is able to replicate and, thus, express the polypeptide encoded by the nucleic acids and elicit an immune response in the infected animal. (See, M. A. Berry et al. in *Nature* (1995), 377; pp/632-635 discloses the preparation of vaccines using nucleic acid molecules).

The vaccines including the nucleic acid encoding the isolated or recombinant YscF or homologs thereof are manufactured by transforming an expression vector including the nucleic acid encoding the isolated or recombinant YscF or homologs thereof into a cell, multiplying the expression vectors and injecting purified expression vectors into a subject. As known by those of ordinary skill in the art, nucleic acid vaccines may comprise expressible DNA or mRNA which may be delivered to cells of the animal to be vaccinated. When the nucleic acid encoding the isolated or recombinant YscF or homologs thereof is operably linked to a promoter expressible in the animal to be vaccinated, the cells of the animal will express the nucleic acid and, thus, include the capability to induce a cell mediated immune response, a humoral immune response or a combination thereof.

EXAMPLE VII

Mice that were immunized with YscF demonstrated a 134-fold increase in the calculated $LD_{50}$ value as compared to PBS immunized mice (Table 1). The increased $LD_{50}$ value demonstrates that immunization with YscF protects mice from lethal challenge with *Y. pestis* KIM5 (Table 1). This result demonstrates that YscF can be developed as a novel vaccine for pathogens of *Yersinia* origin, such as *Y. pestis*, or could serve as another antigen in a multivalent *Yersinia* vaccine including YscF, the F1 antigen, LcrV, and combinations thereof Based on the high degree of homology among YscF proteins originating from strains of *Y. pestis* and *Y. enterocolitica* as illustrated in FIG. 1, the protection conferred by YscF against *Y. pestis* is also expected to confer protection against infections with *Y. enterocolitica* which includes a substantially similar type III secretion system. Further, since many proteins of the type III secretion complex of both *Y. pestis* and *Y. pseudotuberculosis* are substantially similar, the protection conferred by YscF against *Y. pestis* is also expected to confer protection against infections with *Y. pseudotuberculosis*.

TABLE 1

| Immunogen | anti-YscF GMT* | $LD_{50}$ | Fold increase in survival |
|---|---|---|---|
| PBS | <1:400 | 159 | — |
| HT-YscF | 1:40,000 | 21,344 | 134 |

*Geometric mean titer

EXAMPLE VIII

Characterization of the Antibody Response to HT-YscF
Characterization of the antibody response to HT-YscF. Flat-bottom, 96-well Nunc Maxisorp immunoplates (Fisher Scientific, Pittsburgh, Pa.) were coated with 100 µl of HT-YscF solution (4 µg/ml in Binding solution (0.1 M $NaH_2PO_4$, ph 9.0) at room temperature for 2 h (or overnight at 4° C.). The wells were blocked with 200 µl/well blocking buffer (1% bovine serum albumin in TTBS (tris-buffered saline (3)+0.5% Tween 20) and washed with TTBS. Test sera were serially diluted in blocking buffer and 100 µl of each dilution was added to duplicate wells that were incubated for 2 h at RT (or overnight at 4° C.). The plates were washed and incubated for 2 h at RT with alkaline-phosphatase-conjugated anti-mouse secondary antibody. The high antibody response observed against HT-YscF is evidence that YscF is not only expressed during the course of an infection with pathogens of *Yersinia* origin, but also that YscF is in a location accessible to antibodies, such as on the bacterial surface.

For quantitation of YscF-specific immunoglobulin isotypes and subclasses, the plates were coated with alkaline-phosphatase-labeled anti-mouse isotype-specific antibody (1:400 in blocking buffer; Southern Biotech, Birmingham, Ala.). The wells were washed and 75 µl 3 mM para-nitro phenyl phosphate (p-NPP) was added to each well. The plates were incubated for 15 min at RT (room temperature) and the reaction was stopped by the addition of 50 µl of 1.5 M NaOH to each well. $A_{405}$ was measured with a Thermo Max kinetic microplate reader (Molecular Devices Corp., Menlo Park, Calif.) to monitor the cleavage of p-NPP. Antibody titers were determined as reciprocal numbers of the highest serum dilution that displayed values for optical density twofold higher than the value of the control serum.

Anti-YscF antibody titers were determined two weeks following the last immunization, prior to challenge. The YscF-specific antibody titers of PBS-immunized mice were below the ELISA assay baseline of 400 (Table 1), as was the pre-immune serum (data not shown). However, the HT-YscF immunized mice reached a GMT (geometric mean titer) of 40,000 (Table 1). The IgG titer was very high, especially the IgG1 and IgG2b subclasses and the antibody response consisted primarily of antibodies possessing kappa light chains. Interestingly, Titball et al. showed that IgG1 titers to the F1-LcrV chimera correlated very well with protection against pneumonic plague (28). This suggests that YscF may afford protection against pneumonic challenge as well as against systemic challenge.

EXAMPLE IX

Derivatives of *Yersinia pestis* KIM8-3002 (KIM5 pPCP1-minus, Sm$^r$) were grown in a chemically defined medium (17) at 26° C. for 2 h in the presence (lanes 1, 3, and 5) (FIG. 5) or absence of calcium (lanes 2, 4, and 6) (FIG. 5) or the presence of arabinose (lanes 3 and 4) (FIG. 5). pPCP1 is a plasmid originating from *Y. pestis* and has the Medline Accession No. AL109969. (See, Parkhill et al., Genome sequence of *Yersinia pestis*, the causative agent of the plague, Nature 413 (6855), 523-527 (2001)). Lanes 1 and 2 contain *Y. pestis* KIM8-3002. Lanes 3 and 4 contain *Y. pestis* KIM8-3002 expressing YscF from pBAD18-YscF (SEQ ID NO: 20). Lanes 5 and 6 contain *Y. pestis* KIM8-3002 harboring a deletion in the yscF gene. After the 2 h growth, the culture was shifted to 37° C. to induce expression of the Ysc type III secretion system and the Low Calcium Response. Following 4 h of growth at 37° C., cultures were centrifuged to obtain whole cell fractions and cell-free culture supernatant fractions.

Total proteins from each fraction were precipitated with 10% tri-chloro acetic acid. Dried proteins were re-suspended in SDS-PAGE sample buffer and electrophoresed in a 15% SDS-PAGE gel. Proteins were transferred to an Immobilon membrane (Millipore, Bedford, Mass.) and immuno-blotted with pooled mouse serum used at a 1:20,000 dilution. Mouse serum was obtained by bleeding mice subsequent to immunization with HT-YscF. Immunoblots were blocked in 5% non-fat skim milk in 1× Tris-buffered saline plus 0.05% Tween-20 (TTBS). Pooled serum was added to 1% non-fat dry skim milk in 1% TTBS and incubated overnight. Detection of bound antibody was accomplished by incubation with an alkaline phosphatase conjugated goat-anti-mouse antibody. Antibody complexes were visualized by adding NBTBCIP.

Figure 5:
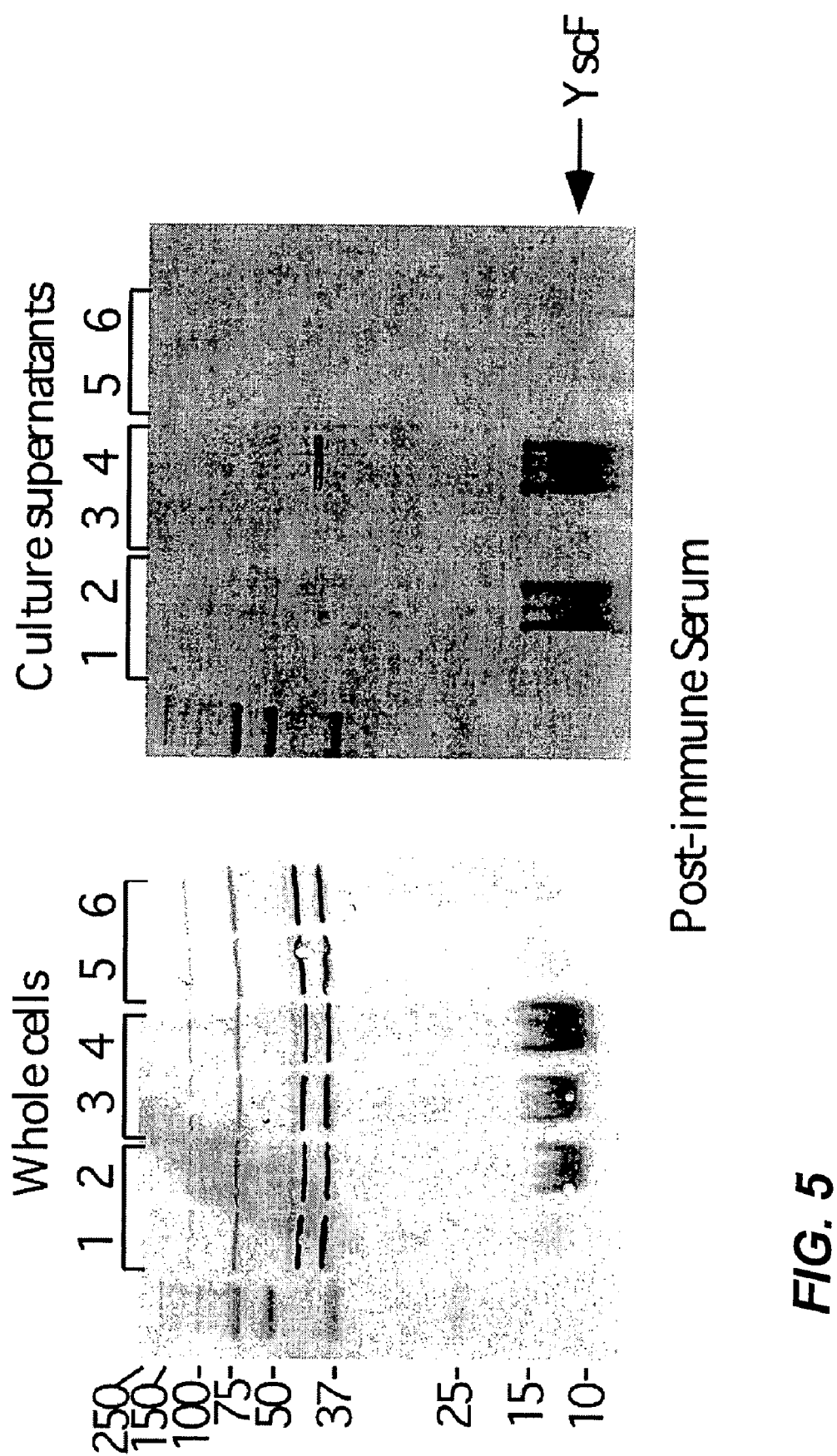
FIG. 5 represents the presence or absence of YscF protein in the culture supernatants of various *Y. pestis* strains.

Serum from several mice were pooled to control for animal specific variation. The position and sizes for the molecular weight markers are indicated and the position of YscF is shown (FIG. 5). As seen in FIG. 5, YscF is visualized on the immunoblot as a highly reactive band of the correct size predicted for YscF and the band is only seen in strains containing the yscF gene. Importantly, no band is seen in lanes 5 and 6 that contain proteins derived from the yscF deletion strain. In lanes 1 and 2, calcium regulation of the YscF band is seen as expected. The higher molecular weight bands seen in the whole cell fraction represent cross-reactive *Y. pestis* bands that are present in samples probed with pre-immune serum (not shown). The higher molecular weight band seen the culture supernatant fractions is consistent with the expected size of an YscF trimer.

EXAMPLE X

In another exemplary embodiment, antibodies or derivatives thereof (e.g., fragments such as Fab, F(ab')$_2$ or Fv fragments), which are directed against isolated or recombinant YscF or homologs thereof are used in passive immunotherapy, diagnostic immunoassays and in the generation of anti-idiotypic antibodies. Serum including polyclonal antibodies of derivatives thereof directed against the isolated or recombinant YscF or homologs thereof is obtained as described herein. Monospecific antibodies directed against the isolated or recombinant YscF or homologs thereof are affinity purified from polyspecific antisera by a modification of the method of Hall et al. (See, Nature, 311, 379-387, 1984).

An epitope of the isolated or recombinant YscF or homologs thereof to which the antibodies bind is determined using known techniques including, but not limited to, Pepscan or microarray technology. When the amino acid residues of the epitope are determined, one skilled in the art generates peptides having amino acid residues of the epitope by artificially synthesizing the peptides of the epitope or using recombinant nucleic acid technology. The synthetic peptides are used to form a composition, vaccine or medicament and used to treat a disease associated with a pathogen of *Yersinia* origin or generating antibodies.

Monoclonal antibodies reactive against the isolated or recombinant YscF or homologs thereof are prepared by immunizing mice using techniques known in the art. (See, Kohler and Milstein, *Nature,* 256, 495-497, 1975). Hybridoma cells are selected by growth in hypoxanthine, thymidine and aminopterin in an appropriate cell culture medium such as Dulbecco's modified Eagle's medium. Antibody producing hybridomas are cloned, such as by using the soft agar technique of MacPherson. (See, Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hydriboma cells are maintained by techniques known in the art and specific antimonoclonal antibodies are produced by cultivating the hydridomas in vitro or preparing ascites fluid in mice following hydridoma injection using procedures known in the art.

Anti-idiotypic antibodies are immunoglobulins which carry an "internal image" of the isolated or recombinant YscF or homologs thereof of the pathogen against which protection is desired and are used as an immunogen in a vaccine as described in Dreesman et al. (See, *J. Infect. Disease,* 151, 741, 1985). Techniques for raising anti-idiotypic antibodies are known in the art. (See, MacNamara et al., *Science* 226, 1325, 1984).

EXAMPLE XI

A diagnostic kit including antibodies generated against isolated or recombinant YscF or homologs thereof for diagnosing disease is also included. The kit contains at least one antibody or fragment thereof directed against the isolated or recombinant YscF or homologs thereof. The immunochemical reaction employed using the kit is a sandwich reaction, an agglutination reaction, a competition reaction or an inhibition reaction, all of which are known by those of ordinary skill in the art. When the kit is used to perform a sandwich reaction, the kit includes isolated or recombinant YscF or homologs thereof bonded to a solid support, such as the inner wall of a tube or well of a plate. The kit is used to detect the presence of isolated or recombinant YscF of *Yersinia* origin or homologs thereof in fleas, mice, rats, prairie dogs, pigs, humans, cats dogs and tissues thereof to ascertain if populations of the animals have been infected with pathogens of *Yersinia* origin.

The exemplary embodiments described herein are not meant to limit the scope of the present invention. The present invention may be carried out using embodiments different from those specifically exemplified herein. Therefore, the scope of the present invention is not limited by the exemplary embodiments, but is defined by the appended claims.

REFERENCES

1. Allaoui, A., R. Schulte, and G. R. Cornelis. 1995. Mutational analysis of the *Yersinia enterocolitica* virC operon: characterization of yscE, F, G, I, J, K required for Yop secretion and yscH encoding YopR. Mol Microbiol 18:343-55.
2. Blocker, A., N. Jouihri, E. Larquet, P. Gounon, F. Ebel, C. Parsot, P. Sansonetti, and A. Allaoui. 2001. Structure and composition of the *Shigella flexneri* "needle complex", a part of its type III secreton. Mol Microbiol 39:652-63.
3. Coligan, J. E., B. M. Dunn, D. W. Speicher, and P. T. Wingfield (ed.). 1998. Current protocols in protein science. John Wiley & Sons, New York.
4. Cornelis, G. R. 2002. The *Yersinia* Ysc-Yop 'type III' weaponry. Nat Rev Mol Cell Biol 3:742-52.
5. Daniell, S. J., N. Takahashi, R. Wilson, D. Friedberg, I. Rosenshine, F. P. Booy, R. K. Shaw, S. Knutton, G. Frankel, and S. Aizawa. 2001. The filamentous type III secretion translocon of enteropathogenic *Escherichia coli.* Cell Microbiol 3:865-71.
6. Davis, K. J., D. L. Fritz, M. L. Pitt, S. L. Welkos, P. L. Worsham, and A. M. Friedlander. 1996. Pathology of experimental pneumonic plague produced by fraction 1-positive and fraction 1-negative *Yersinia pestis* in African green monkeys (*Cercopithecus aethiops*). Arch Pathol Lab Med 120:156-63.
7. Drozdov, I. G., A. P. Anisimov, S. V. Samoilova, I. N. Yezhov, S. A. Yeremin, A. V. Karlyshev, V. M. Krasilnikova, and V. I. Kravchenko. 1995. Virulent non-capsulate *Yersinia pestis* variants constructed by insertion mutagenesis. J Med Microbiol 42:264-8.
8. Du, Y., E. Galyov, and A. Forsberg. 1995. Genetic analysis of virulence determinants unique to *Yersinia pestis*. Contrib Microbiol Immunol 13:321-4.
9. Fields, K. A., M. L. Nilles, C. Cowan, and S. C. Straley. 1999. Virulence role of V antigen of *Yersinia pestis* at the bacterial surface. Infection and Immunity 67:5395-408.
10. Haddix, P. L., and S. C. Straley. 1992. Structure and regulation of the *Yersinia pestis* yscBCDEF operon. J Bacteriol 174:4820-8.
11. Håkansson, S., K. Schesser, C. Persson, E. E. Galyov, R. Rosqvist, F. Homblé, and H. Wolf-Watz. 1996. The YopB protein of *Yersinia pseudotuberculosis* is essential for the translocation of Yop effector proteins across the target cell plasma membrane and displays a contact-dependent membrane disrupting activity. EMBO Journal 15:5812-5823.
12. Hoiczyk, E., and G. Blobel. 2001. Polymerization of a single protein of the pathogen *Yersinia enterocolitica* into needles punctures eukaryotic cells. Proc Natl Acad Sci USA 98:4669-74.
13. Holmström, A., J. Olsson, P. Cherepanov, E. Maier, R. Nordfelth, J. Pettersson, R. Benz, H. Wolf-Watz, and A. A. Forsberg. 2001. LcrV is a channel size-determining component of the Yop effector translocon of *Yersinia*. Mol Microbiol 39:620-632.
14. Inglesby, T. V., D. T. Dennis, D. A. Henderson, J. G. Bartlett, M. S. Ascher, E. Eitzen, A. D. Fine, A. M. Friedlander, J. Hauer, J. F. Koerner, M. Layton, J. McDade, M. T. Osterholm, T. O'Toole, G. Parker, T. M. Perl, P. K. Russell, M. Schoch-Spana, and K. Tonat. 2000. Plague as a biological weapon: medical and public health management. Working Group on Civilian Biodefense. Jama 283:2281-90.
15. Kubori, T., Y. Matsushima, D. Nakamura, J. Uralil, M. Lara-Tejero, A. Sukhan, J. E. Galan, and S.-I. Aizawa. 1998. Supramolecular structure of the *Salmonella typhimurium* type III protein secretion system. Science 280: 602-605.
16. Kubori, T., A. Sukhan, S. I. Aizawa, and J. E. Galan. 2000. Molecular characterization and assembly of the needle complex of the *Salmonella typhimurium* type III protein secretion system. Proc Natl Acad Sci USA 97:10225-30.
17. Nines, M. L., K. A. Fields, and S. C. Straley. 1998. The V antigen of *Yersinia pestis* regulates Yop vectorial targeting as well as Yop secretion through effects on YopB and LcrG. Journal of Bacteriology 180:3410-3420.
18. Nordfelth, R., and H. Wolf-Watz. 2001. YopB of *Yersinia enterocolitica* Is Essential for YopE Translocation. Infect Immun 69:3516-8.
19. Perry, R. D., and J. D. Fetherson. 1997. *Yersinia pestis*—etiologic agent of plague. Clinical Microbiology Reviews 10:35-66.
20. Perry, R. D., S. C. Straley, J. D. Fetherston, D. J. Rose, J. Gregor, and F. R. Blattner. 1998. DNA sequencing and analysis of the low-$Ca^{2+}$-response plasmid pCD1 of *Yersinia pestis* KIM5. Infection and Immunity 66:4611-4623.
21. Pettersson, J., A. Holmström, J. Hill, S. Leary, E. Frithz-Lindsten, A. von Euler-Matell, E. Carlsson, R. Titball, Å. Forsberg, and H. Wolf-Watz. 1999. The V-antigen of *Yersinia* is surface-exposed before target cell contact and involved in virulence protein translocation. Molecular Microbiology 32:961-976.
22. Sekiya, K., M. Ohishi, T. Ogino, K. Tamano, C. Sasakawa, and A. Abe. 2001. Supermolecular structure of the enteropathogenic *Escherichia coli* type III secretion system and its direct interaction with the EspA-sheath-like structure. Proc Natl Acad Sci USA 98:11638-43.
23. Sory, M.-P., and G. R. Cornelis. 1994. Translocation of a hybrid YopE-adenylate cyclase from *Yersinia enterocolitica* into HeLa cells. Molecular Microbiology 14:583-594.
24. Tardy, F., F. Homblé, C. Neyt, R. Wattiez, G. R. Cornelis, J.-M. Ruysschaert, and V. Cabiaux. 1999. *Yersinia enterocolitica* type III secretion-translocation system: channel formation by secreted Yops. EMBO Journal 18:6793-6799.
25. Titball, R. W., and E. D. Williamson. 2001. Vaccination against bubonic and pneumonic plague. Vaccine 19:4175-84.
26. Welkos, S., and A. O'Brien. 1994. Determination of median lethal and infectious doses in animal model systems. Methods Enzymol 235:29-39.
27. Welkos, S. L., K. M. Davis, L. M. Pitt, P. L. Worsham, and A. M. Freidlander. 1995. Studies on the contribution of the F1 capsule-associated plasmid pFra to the virulence of *Yersinia pestis*. Contrib Microbiol Immunol 13:299-305.
28. Williamson, E. D., P. M. Vesey, K. J. Gillhespy, S. M. Eley, M. Green, and R. W. Titball. 1999. An IgG1 titre to the F1 and V antigens correlates with protection against plague in the mouse model. Clin Exp Immunol 116:107-14.
29. Wilson, R. K., R. K. Shaw, S. Daniell, S. Knutton, and G. Frankel. 2001. Role of EscF, a putative needle complex protein, in the type III protein translocation system of enteropathogenic *Escherichia coli*. Cell Microbiol 3:753-62.

SEQUENCE LISTING

<160> NUMBER OF SEQ ID NOS: 20

<210> SEQ ID NO 1
<211> LENGTH: 87
<212> TYPE: PRT
<213> ORGANISM: Yersinia pestis
<220> FEATURE:
<223> OTHER INFORMATION: amino acid sequence of YscF
<220> FEATURE:

-continued

```
<223> OTHER INFORMATION: sequence can be found at MedLine accession
      number NP_857921.1

<400> SEQUENCE: 1

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 2
<211> LENGTH: 264
<212> TYPE: DNA
<213> ORGANISM: Yersinia pestis
<220> FEATURE:
<223> OTHER INFORMATION: nucliec acids encoding YscF
<220> FEATURE:
<223> OTHER INFORMATION: sequence can be found at MedLine accession
      number NL_004839

<400> SEQUENCE: 2
atgagtaact tctctggatt tacgaaagga accgatatcg cagacttaga tgcggtggct     60
caaacgctca agaagccagc agacgatgca aacaaagcgg ttaatgactc gatagcagca    120
ttgaaagata agcctgacaa cccggcgcta cttgctgact tacaacattc aattaataaa    180
tggtcggtaa tttacaatat aaactcaacc atagttcgta gcatgaaaga cttaatgcaa    240
ggcatcctac agaagttccc ataa                                           264

<210> SEQ ID NO 3
<211> LENGTH: 264
<212> TYPE: DNA
<213> ORGANISM: Yersinia enterocolitica
<220> FEATURE:
<223> OTHER INFORMATION: nucleic acid encoding YscF from
      Y. enterocolitica
<220> FEATURE:
<223> OTHER INFORMATION: sequence can be found at MedLine accession
      number NC_005017

<400> SEQUENCE: 3
atgagtaatt tctctgggtt tgcaaaagga accgatatca cagacttaga tgcggtggct     60
caaacgctca agaagccagc agacggcgca aacaaagcgg ttaatgactc gatagcagcg    120
ttgaaagaga cgcctgacaa cccggcgcta cttgctgact tacaacattc aattaataaa    180
tggtcggtaa tttacaatat aagctcaacc atagttcgta gcatgaaaga cttaatgcaa    240
ggcatcctac agaagttccc ataa                                           264

<210> SEQ ID NO 4
<211> LENGTH: 87
<212> TYPE: PRT
<213> ORGANISM: Yersinia enterocolitica
<220> FEATURE:
<223> OTHER INFORMATION: amino acid sequence of YscF from
      Y. enterocolitica
<220> FEATURE:
```

<223> OTHER INFORMATION: sequence can be found at MedLine accession
      number NP_863538.1

<400> SEQUENCE: 4

Met Ser Asn Phe Ser Gly Phe Ala Lys Gly Thr Asp Ile Thr Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Thr Pro Asp Asn Pro
        35                  40                  45

Ala Leu Leu Ala Asp Leu Gln His Ser Ile Asn Lys Trp Ser Val Ile
    50                  55                  60

Tyr Asn Met Ser Ser Thr Ile Val Arg Ser Met Lys Asp Leu Met Gln
65                  70                  75                  80

Gly Ile Leu Gln Lys Phe Pro
                85

<210> SEQ ID NO 5
<211> LENGTH: 80
<212> TYPE: PRT
<213> ORGANISM: Salmonella enterica
<220> FEATURE:
<223> OTHER INFORMATION: amino acid sequence of PrgI
<220> FEATURE:
<223> OTHER INFORMATION: sequence can be found at MedLine accession
      number CAD05980.1

<400> SEQUENCE: 5

Met Pro Thr Ser Trp Ser Gly Tyr Leu Asp Glu Val Ser Ala Lys Phe
1               5                   10                  15

Asp Lys Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gln Asn Phe Arg
65                  70                  75                  80

<210> SEQ ID NO 6
<211> LENGTH: 243
<212> TYPE: DNA
<213> ORGANISM: Salmonella enterica
<220> FEATURE:
<223> OTHER INFORMATION: sequence can be found at MedLine accession
      number AL627276
<220> FEATURE:
<223> OTHER INFORMATION: nucleic acid encoding PrgI

<400> SEQUENCE: 6
atgccaacat cttggtcagg ctatctggat gaagtttcag caaaatttga taagggcgtt      60
gataatctac aaacgcaggt aacagaggcg ctggataaat tagcagcaaa accctccgat     120
ccggcgctac tggcggcgta tcagagtaag ctctcggaat ataacttgta ccgtaacgcg     180
caatcgaaca cggtaaaagt ctttaaggat attgatgctg ccattattca gaacttccgt     240
taa                                                                    243

<210> SEQ ID NO 7
<211> LENGTH: 83
<212> TYPE: PRT
<213> ORGANISM: Shigella flexneri
<220> FEATURE:
<223> OTHER INFORMATION: amino acid sequence of MxiH
<220> FEATURE:
<223> OTHER INFORMATION: sequence can be found at MedLine accession
    number NP_858270.1

<400> SEQUENCE: 7

Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg

<210> SEQ ID NO 8
<211> LENGTH: 252
<212> TYPE: DNA
<213> ORGANISM: Shigella flexneri
<220> FEATURE:
<223> OTHER INFORMATION: nucleic acid encoding MxiH
<220> FEATURE:
<223> OTHER INFORMATION: sequence can be found at MedLine accession
    number Nc_004851

<400> SEQUENCE: 8
atgagtgtta cagtaccgaa tgatgattgg acattgagtt cattatctga aactttttgat    60 gatggaactc aaacattaca aggtgaacta acattggcac tagataaatt agctaaaaat   120
ccttcgaatc cacagttgct ggctgaatac caaagtaaat tatctgaata tacattatat   180
aggaacgcgc aatccaatac agtgaaagtg attaaggatg ttgatgctgc aattattcaa   240
aacttcagat aa                                                        252

<210> SEQ ID NO 9
<211> LENGTH: 73
<212> TYPE: PRT
<213> ORGANISM: Escherichia coli
<220> FEATURE:
<223> OTHER INFORMATION: amino acid sequence of EscF
<220> FEATURE:
<223> OTHER INFORMATION: sequence can be found at MedLine accession
    number NP_312579.1

<400> SEQUENCE: 9

Met Asn Leu Ser Glu Ile Thr Gln Gln Met Gly Glu Val Gly Lys Thr
1               5                   10                  15

Leu Ser Asp Ser Val Pro Glu Leu Leu Asn Ser Thr Asp Leu Val Asn
            20                  25                  30

Asp Pro Glu Lys Met Leu Glu Leu Gln Phe Ala Val Gln Gln Tyr Ser
        35                  40                  45

Ala Tyr Val Asn Val Glu Ser Gly Met Leu Lys Thr Ile Lys Asp Leu
    50                  55                  60

Val Ser Thr Ile Ser Asn Arg Ser Phe
65                  70

<210> SEQ ID NO 10
<211> LENGTH: 222

<212> TYPE: DNA
<213> ORGANISM: Escherichia coli
<220> FEATURE:
<223> OTHER INFORMATION: nucleic acid encoding EscF
<220> FEATURE:
<223> OTHER INFORMATION: sequence can be found at MedLine accession
      number NC_002695

<400> SEQUENCE: 10
atgaatttat ctgaaattac tcaacaaatg ggtgaagtag gtaaaacgct gagcgattct    60
gtgccagagt tacttaatag caccgatttg gttaatgacc ctgaaaaaat gttagagttg   120
cagtttgcgg ttcagcaata ttctgcttat gttaacgtag aaagtggaat gttgaaaacg   180
ataaaagatc tggtctcaac catttctaac cgtagttttt aa                      222

<210> SEQ ID NO 11
<211> LENGTH: 240
<212> TYPE: DNA
<213> ORGANISM: Yersinia pestis
<220> FEATURE:
<223> OTHER INFORMATION: nucleic acid encoding HT-YscF; an example of a
      recombinant YscF
<220> FEATURE:
<221> NAME/KEY: misc_feature
<222> LOCATION: (214)..(237)
<223> OTHER INFORMATION: His-tag sequence

<400> SEQUENCE: 11
atgagtaact tctctggatt tacgaaagga accgatgatg caaacaaagc ggttaatgac    60
tcgatagcag cattgaaaga taagcctgac aacccggcgc tacttgctga cttacaacat   120
tcaattaata aatggtcggt aatttacaat ataaactcaa ccatagttcg tagcatgaaa   180
gacttaatgc aaggcatcct acagaagttc ccactcgagc accaccacca ccaccactga   240

<210> SEQ ID NO 12
<211> LENGTH: 95
<212> TYPE: PRT
<213> ORGANISM: Yersinia pestis
<220> FEATURE:
<223> OTHER INFORMATION: amino acid sequence of HT-YscF; an example of a
      recombinant YscF
<220> FEATURE:
<221> NAME/KEY: misc_feature
<222> LOCATION: (88)..(95)
<223> OTHER INFORMATION: His-tag

<400> SEQUENCE: 12

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro Leu Glu His His His His His
                85                  90                  95

<210> SEQ ID NO 13
<211> LENGTH: 5537
<212> TYPE: DNA
<213> ORGANISM: Artificial Sequence

```
<220> FEATURE:
<223> OTHER INFORMATION: pMJ119
<220> FEATURE:
<221> NAME/KEY: misc_feature
<222> LOCATION: (563)..(1375)
<223> OTHER INFORMATION: kan encoded on complementary strand
<220> FEATURE:
<221> NAME/KEY: misc_feature
<222> LOCATION: (3518)..(4597)
<223> OTHER INFORMATION: LacI encoded on complementary strand
<220> FEATURE:
<221> NAME/KEY: promoter
<222> LOCATION: (4983)..(5000)
<223> OTHER INFORMATION: T7 promoter
<220> FEATURE:
<221> NAME/KEY: misc_feature
<222> LOCATION: (5001)..(5001)
<223> OTHER INFORMATION: T7 transcription start
<220> FEATURE:
<221> NAME/KEY: misc_feature
<222> LOCATION: (5072)..(5104)
<223> OTHER INFORMATION: T7 Tag
<220> FEATURE:
<221> NAME/KEY: CDS
<222> LOCATION: (5114)..(5401)
<223> OTHER INFORMATION: HT-YscF
<220> FEATURE:
<221> NAME/KEY: misc_feature
<222> LOCATION: (5381)..(5398)
<223> OTHER INFORMATION: His-tag sequence
<220> FEATURE:
<221> NAME/KEY: terminator
<222> LOCATION: (5466)..(5512)
<223> OTHER INFORMATION: T7 terminator

<400> SEQUENCE: 13
```

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aacccatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttattttc | taaatacatt | caaatatgta | 540 |
| tccgctcatg | aattaattct | tagaaaaact | catcgagcat | caaatgaaac | tgcaattat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |

```
tcgcacctga ttgcccgaca ttatcgcgag cccatttata cccatataaa tcagcatcca      1320
tgttggaatt taatcgcggc ctagagcaag acgtttcccg ttgaatatgg ctcataacac      1380
cccttgtatt actgtttatg taagcagaca gttttattgt tcatgaccaa aatcccttaa     1440
cgtgagtttt cgttccactg agcgtcagac cccgtagaaa agatcaaagg atcttcttga      1500
gatccttttt ttctgcgcgt aatctgctgc ttgcaaacaa aaaaaccacc gctaccagcg      1560
gtggtttgtt tgccggatca agagctacca actcttttc cgaaggtaac tggcttcagc      1620
agagcgcaga taccaaatac tgtccttcta gtgtagccgt agttaggcca ccacttcaag      1680
aactctgtag caccgcctac atacctcgct ctgctaatcc tgttaccagt ggctgctgcc      1740
agtggcgata agtcgtgtct taccgggttg gactcaagac gatagttacc ggataaggcg      1800
cagcggtcgg gctgaacggg gggttcgtgc acacagccca gcttggagcg aacgacctac      1860
accgaactga atacctaca gcgtgagcta tgagaaagcg ccacgcttcc cgaagggaga      1920
aaggcggaca ggtatccggt aagcggcagg gtcggaacag gagagcgcac gagggagctt      1980
ccagggggaa acgcctggta tctttatagt cctgtcgggt ttcgccacct ctgacttgag      2040
cgtcgatttt tgtgatgctc gtcagggggg cggagcctat ggaaaaacgc cagcaacgcg      2100 gccttttta c ggttcctggc cttttgctgg ccttttgctc acatgttctt tcctgcgtta      2160
tcccctgatt ctgtggataa ccgtattacc gcctttgagt gagctgatac cgctcgccgc      2220
agccgaacga ccgagcgcag cgagtcagtg agcgaggaag cggaagagcg cctgatgcgg      2280
tattttctcc ttacgcatct gtgcggtatt tcacaccgca tatatggtgc actctcagta      2340
caatctgctc tgatgccgca tagttaagcc agtatacact ccgctatcgc tacgtgactg      2400
ggtcatggct gcgccccgac acccgccaac acccgctgac gcgccctgac gggcttgtct      2460
gctcccggca tccgcttaca gacaagctgt gaccgtctcc gggagctgca tgtgtcagag      2520
gttttcaccg tcatcaccga aacgcgcgag gcagctgcgg taaagctcat cagcgtggtc      2580
gtgaagcgat tcacagatgt ctgcctgttc atccgcgtcc agctcgttga gtttctccag      2640
aagcgttaat gtctggcttc tgataaagcg ggccatgtta agggcggttt tttcctgttt      2700
ggtcactgat gcctccgtgt aagggggatt tctgttcatg ggggtaatga taccgatgaa      2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
tcaatgccag cgcttcgtta atacagatgt aggtgttcca cagggtagcc agcagcatcc      2940
tgcgatgcag atccggaaca taatggtgca gggcgctgac ttccgcgttt ccagacttta      3000
cgaaacacgg aaaccgaaga ccattcatgt tgttgctcag gtcgcagacg ttttgcagca      3060
gcagtcgctt cacgttcgct cgcgtatcgg tgattcattc tgctaaccag taaggcaacc      3120
ccgccagcct agccgggtcc tcaacgacag gagcacgatc atgcgcaccc gtggggccgc      3180
catgccggcg ataatggcct gcttctcgcc gaaacgtttg gtggcgggac cagtgacgaa      3240
ggcttgagcg agggcgtgca agattccgaa taccgcaagc gacaggccga tcatcgtcgc      3300
gctccagcga aagcggtcct cgccgaaaat gacccagagc gctgccggca cctgtcctac      3360
gagttgcatg ataaagaaga cagtcataag tgcggcgacg atagtcatgc cccgcgccca      3420
ccggaaggag ctgactgggt tgaaggctct caagggcatc ggtcgagatc ccggtgccta      3480
atgagtgagc taacttacat taattgcgtt gcgctcactg cccgctttcc agtcgggaaa      3540
cctgtcgtgc cagctgcatt aatgaatcgg ccaacgcgcg gggagaggcg gtttgcgtat      3600
tgggcgccag ggtggttttt cttttcacca gtgagacggg caacagctga ttgcccttca      3660
```

```
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggctagc atgactggtg gacagcaaat    5100
gggtcgggat ccg atg agt aac ttc tct gga ttt acg aaa gga acc gat      5149
                Met Ser Asn Phe Ser Gly Phe Thr Lys Gly Thr Asp
                 1               5                  10 atc gca gac tta gat gcg gtg gct caa acg ctc aag aag cca gca gac      5197
Ile Ala Asp Leu Asp Ala Val Ala Gln Thr Leu Lys Lys Pro Ala Asp
         15                  20                  25 gat gca aac aaa gcg gtt aat gac tcg ata gca gca ttg aaa gat aag      5245
Asp Ala Asn Lys Ala Val Asn Asp Ser Ile Ala Ala Leu Lys Asp Lys
     30                  35                  40 cct gac aac ccg gcg cta ctt gct gac tta caa cat tca att aat aaa      5293
Pro Asp Asn Pro Ala Leu Leu Ala Asp Leu Gln His Ser Ile Asn Lys
45                  50                  55                  60 tgg tcg gta att tac aat ata aac tca acc ata gtt cgt agc atg aaa      5341
Trp Ser Val Ile Tyr Asn Ile Asn Ser Thr Ile Val Arg Ser Met Lys
                 65                  70                  75 gac tta atg caa ggc atc cta cag aag ttc cca ctc gag cac cac cac      5389
Asp Leu Met Gln Gly Ile Leu Gln Lys Phe Pro Leu Glu His His His
         80                  85                  90 cac cac cac tga gatccggctg ctaacaaagc ccgaaggaa gctgagttgg           5441
His His His
     95 ctgctgccac cgctgagcaa taactagcat aaccccttgg ggcctctaaa cgggtcttga    5501
``` ggggttttttt gctgaaagga ggaactatat ccggat 5537

<210> SEQ ID NO 14
<211> LENGTH: 5309
<212> TYPE: DNA
<213> ORGANISM: Artificial Sequence
<220> FEATURE:
<223> OTHER INFORMATION: pET24b
<220> FEATURE:
<221> NAME/KEY: terminator
<222> LOCATION: (26)..(72)
<223> OTHER INFORMATION: T7 terminator
<220> FEATURE:
<221> NAME/KEY: misc_feature
<222> LOCATION: (140)..(157)
<223> OTHER INFORMATION: His-tag sequence
<220> FEATURE:
<221> NAME/KEY: misc_feature
<222> LOCATION: (206)..(238)
<223> OTHER INFORMATION: T7 Tag
<220> FEATURE:
<221> NAME/KEY: misc_feature
<222> LOCATION: (309)..(309)
<220> FEATURE:
<221> NAME/KEY: misc_feature
<222> LOCATION: (309)..(309)
<223> OTHER INFORMATION: T7 transcription start
<220> FEATURE:
<221> NAME/KEY: promoter
<222> LOCATION: (310)..(327)
<223> OTHER INFORMATION: T7 promoter
<220> FEATURE:
<221> NAME/KEY: misc_feature
<222> LOCATION: (713)..(716)
<223> OTHER INFORMATION: Alternate start codon "gtg"
<220> FEATURE:
<221> NAME/KEY: CDS
<222> LOCATION: (713)..(1792)
<223> OTHER INFORMATION: lacI
<220> FEATURE:
<221> NAME/KEY: CDS
<222> LOCATION: (3935)..(4747)
<223> OTHER INFORMATION: kan

<400> SEQUENCE: 14

| | | |
|---|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgacggagct cgaattcgga tcccgaccca tttgctgtcc accagtcatg ctagccatat | 240 |
| gtatatctcc ttcttaaagt taaacaaaat tatttctaga ggggaattgt tatccgctca | 300 |
| caattcccct atagtgagtc gtattaattt cgcgggatcg agatctcgat cctctacgcc | 360 |
| ggacgcatcg tggccggcat caccggcgcc acaggtgcgg ttgctggcgc ctatatcgcc | 420 |
| gacatcaccg atggggaaga tcgggctcgc cacttcgggc tcatgagcgc ttgtttcggc | 480 |
| gtgggtatgg tggcaggccc cgtggccggg ggactgttgg gcgccatctc cttgcatgca | 540 |
| ccattccttg cggcggcggt gctcaacggc ctcaacctac tactgggctg cttcctaatg | 600 |
| caggagtcgc ataagggaga gcgtcgagat cccggacacc atcgaatggc gcaaaacctt | 660 |
| tcgcggtatg gcatgatagc gcccggaaga gagtcaattc agggtggtga at gtg aaa | 718 |
|  |  | Met Lys |
|  |  | 1 |
| cca gta acg tta tac gat gtc gca gag tat gcc ggt gtc tct tat cag | 766 |
| Pro Val Thr Leu Tyr Asp Val Ala Glu Tyr Ala Gly Val Ser Tyr Gln |  |
| 5 10 15 |  |
| acc gtt tcc cgc gtg gtg aac cag gcc agc cac gtt tct gcg aaa acg | 814 |
| Thr Val Ser Arg Val Val Asn Gln Ala Ser His Val Ser Ala Lys Thr |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 20  |     |     |     |     | 25  |     |     |     |     | 30  |     |     |     |      |
| cgg | gaa | aaa | gtg | gaa | gcg | gcg | atg | gcg | gag | ctg | aat | tac | att | ccc | aac | 862  |
| Arg | Glu | Lys | Val | Glu | Ala | Ala | Met | Ala | Glu | Leu | Asn | Tyr | Ile | Pro | Asn |      |
| 35  |     |     |     |     | 40  |     |     |     |     | 45  |     |     |     |     | 50  |      |
| cgc | gtg | gca | caa | caa | ctg | gcg | ggc | aaa | cag | tcg | ttg | ctg | att | ggc | gtt | 910  |
| Arg | Val | Ala | Gln | Gln | Leu | Ala | Gly | Lys | Gln | Ser | Leu | Leu | Ile | Gly | Val |      |
|     |     |     |     | 55  |     |     |     |     | 60  |     |     |     |     | 65  |     |      |
| gcc | acc | tcc | agt | ctg | gcc | ctg | cac | gcg | ccg | tcg | caa | att | gtc | gcg | gcg | 958  |
| Ala | Thr | Ser | Ser | Leu | Ala | Leu | His | Ala | Pro | Ser | Gln | Ile | Val | Ala | Ala |      |
|     |     |     | 70  |     |     |     |     | 75  |     |     |     |     | 80  |     |     |      |
| att | aaa | tct | cgc | gcc | gat | caa | ctg | ggt | gcc | agc | gtg | gtg | gtg | tcg | atg | 1006 |
| Ile | Lys | Ser | Arg | Ala | Asp | Gln | Leu | Gly | Ala | Ser | Val | Val | Val | Ser | Met |      |
|     |     | 85  |     |     |     |     | 90  |     |     |     |     | 95  |     |     |     |      |
| gta | gaa | cga | agc | ggc | gtc | gaa | gcc | tgt | aaa | gcg | gcg | gtg | cac | aat | ctt | 1054 |
| Val | Glu | Arg | Ser | Gly | Val | Glu | Ala | Cys | Lys | Ala | Ala | Val | His | Asn | Leu |      |
| 100 |     |     |     |     | 105 |     |     |     |     | 110 |     |     |     |     |     |      |
| ctc | gcg | caa | cgc | gtc | agt | ggg | ctg | atc | att | aac | tat | ccg | ctg | gat | gac | 1102 |
| Leu | Ala | Gln | Arg | Val | Ser | Gly | Leu | Ile | Ile | Asn | Tyr | Pro | Leu | Asp | Asp |      |
| 115 |     |     |     |     | 120 |     |     |     |     | 125 |     |     |     |     | 130 |      |
| cag | gat | gcc | att | gct | gtg | gaa | gct | gcc | tgc | act | aat | gtt | ccg | gcg | tta | 1150 |
| Gln | Asp | Ala | Ile | Ala | Val | Glu | Ala | Ala | Cys | Thr | Asn | Val | Pro | Ala | Leu |      |
|     |     |     |     | 135 |     |     |     |     | 140 |     |     |     |     | 145 |     |      |
| ttt | ctt | gat | gtc | tct | gac | cag | aca | ccc | atc | aac | agt | att | att | ttc | tcc | 1198 |
| Phe | Leu | Asp | Val | Ser | Asp | Gln | Thr | Pro | Ile | Asn | Ser | Ile | Ile | Phe | Ser |      |
|     |     |     | 150 |     |     |     |     | 155 |     |     |     |     | 160 |     |     |      |
| cat | gaa | gac | ggt | acg | cga | ctg | ggc | gtg | gag | cat | ctg | gtc | gca | ttg | ggt | 1246 |
| His | Glu | Asp | Gly | Thr | Arg | Leu | Gly | Val | Glu | His | Leu | Val | Ala | Leu | Gly |      |
|     |     | 165 |     |     |     |     | 170 |     |     |     |     | 175 |     |     |     |      |
| cac | cag | caa | atc | gcg | ctg | tta | gcg | ggc | cca | tta | agt | tct | gtc | tcg | gcg | 1294 |
| His | Gln | Gln | Ile | Ala | Leu | Leu | Ala | Gly | Pro | Leu | Ser | Ser | Val | Ser | Ala |      |
| 180 |     |     |     |     | 185 |     |     |     |     | 190 |     |     |     |     |     |      |
| cgt | ctg | cgt | ctg | gct | ggc | tgg | cat | aaa | tat | ctc | act | cgc | aat | caa | att | 1342 |
| Arg | Leu | Arg | Leu | Ala | Gly | Trp | His | Lys | Tyr | Leu | Thr | Arg | Asn | Gln | Ile |      |
| 195 |     |     |     |     | 200 |     |     |     |     | 205 |     |     |     |     | 210 |      |
| cag | ccg | ata | gcg | gaa | cgg | gaa | ggc | gac | tgg | agt | gcc | atg | tcc | ggt | ttt | 1390 |
| Gln | Pro | Ile | Ala | Glu | Arg | Glu | Gly | Asp | Trp | Ser | Ala | Met | Ser | Gly | Phe |      |
|     |     |     |     | 215 |     |     |     |     | 220 |     |     |     |     | 225 |     |      |
| caa | caa | acc | atg | caa | atg | ctg | aat | gag | ggc | atc | gtt | ccc | act | gcg | atg | 1438 |
| Gln | Gln | Thr | Met | Gln | Met | Leu | Asn | Glu | Gly | Ile | Val | Pro | Thr | Ala | Met |      |
|     |     |     | 230 |     |     |     |     | 235 |     |     |     |     | 240 |     |     |      |
| ctg | gtt | gcc | aac | gat | cag | atg | gcg | ctg | ggc | gca | atg | cgc | gcc | att | acc | 1486 |
| Leu | Val | Ala | Asn | Asp | Gln | Met | Ala | Leu | Gly | Ala | Met | Arg | Ala | Ile | Thr |      |
|     |     | 245 |     |     |     |     | 250 |     |     |     |     | 255 |     |     |     |      |
| gag | tcc | ggg | ctg | cgc | gtt | ggt | gcg | gat | atc | tcg | gta | gtg | gga | tac | gac | 1534 |
| Glu | Ser | Gly | Leu | Arg | Val | Gly | Ala | Asp | Ile | Ser | Val | Val | Gly | Tyr | Asp |      |
| 260 |     |     |     |     | 265 |     |     |     |     | 270 |     |     |     |     |     |      |
| gat | acc | gaa | gac | agc | tca | tgt | tat | atc | ccg | ccg | tta | acc | acc | atc | aaa | 1582 |
| Asp | Thr | Glu | Asp | Ser | Ser | Cys | Tyr | Ile | Pro | Pro | Leu | Thr | Thr | Ile | Lys |      |
| 275 |     |     |     |     | 280 |     |     |     |     | 285 |     |     |     |     | 290 |      |
| cag | gat | ttt | cgc | ctg | ctg | ggg | caa | acc | agc | gtg | gac | cgc | ttg | ctg | caa | 1630 |
| Gln | Asp | Phe | Arg | Leu | Leu | Gly | Gln | Thr | Ser | Val | Asp | Arg | Leu | Leu | Gln |      |
|     |     |     |     | 295 |     |     |     |     | 300 |     |     |     |     | 305 |     |      |
| ctc | tct | cag | ggc | cag | gcg | gtg | aag | ggc | aat | cag | ctg | ttg | ccc | gtc | tca | 1678 |
| Leu | Ser | Gln | Gly | Gln | Ala | Val | Lys | Gly | Asn | Gln | Leu | Leu | Pro | Val | Ser |      |
|     |     |     | 310 |     |     |     |     | 315 |     |     |     |     | 320 |     |     |      |
| ctg | gtg | aaa | aga | aaa | acc | acc | ctg | gcg | ccc | aat | acg | caa | acc | gcc | tct | 1726 |
| Leu | Val | Lys | Arg | Lys | Thr | Thr | Leu | Ala | Pro | Asn | Thr | Gln | Thr | Ala | Ser |      |
|     |     | 325 |     |     |     |     | 330 |     |     |     |     | 335 |     |     |     |      |
| ccc | cgc | gcg | ttg | gcc | gat | tca | tta | atg | cag | ctg | gca | cga | cag | gtt | tcc | 1774 |

-continued

```
Pro Arg Ala Leu Ala Asp Ser Leu Met Gln Leu Ala Arg Gln Val Ser
    340                 345                 350 cga ctg gaa agc ggg cag tgagcgcaac gcaattaatg taagttagct        1822
Arg Leu Glu Ser Gly Gln
355                 360 cactcattag gcaccgggat ctcgaccgat gcccttgaga gccttcaacc cagtcagctc   1882
cttccggtgg gcgcggggca tgactatcgt cgccgcactt atgactgtct tctttatcat   1942
gcaactcgta ggacaggtgc cggcagcgct ctgggtcatt ttcggcgagg accgctttcg   2002
ctggagcgcg acgatgatcg gcctgtcgct tgcggtattc ggaatcttgc acgccctcgc   2062
tcaagccttc gtcactggtc ccgccaccaa acgtttcggc gagaagcagg ccattatcgc   2122
cggcatggcg gccccacggg tgcgcatgat cgtgctcctg tcgttgagga cccggctagg   2182
ctggcgggt tgccttactg gttagcagaa tgaatcaccg atacgcgagc gaacgtgaag   2242
cgactgctgc tgcaaaacgt ctgcgacctg agcaacaaca tgaatggtct tcggtttccg   2302
tgtttcgtaa agtctggaaa cgcggaagtc agcgccctgc accattatgt tccggatctg   2362
catcgcagga tgctgctggc taccctgtgg aacacctaca tctgtattaa cgaagcgctg   2422
gcattgaccc tgagtgattt ttctctggtc ccgccgcatc cataccgcca gttgtttacc   2482
ctcacaacgt tccagtaacc gggcatgttc atcatcagta accgtatcg tgagcatcct   2542
ctctcgtttc atcggtatca ttaccccat gaacagaaat cccccttaca cggaggcatc   2602
agtgaccaaa caggaaaaaa ccgcccttaa catggcccgc tttatcagaa gccagacatt   2662
aacgcttctg gagaaactca acgagctgga cgcggatgaa caggcagaca tctgtgaatc   2722
gcttcacgac cacgctgatg agctttaccg cagctgcctc gcgcgtttcg gtgatgacgg   2782
tgaaaacctc tgacacatgc agctcccgga cacggtcaca gcttgtctgt aagcggatgc   2842
cgggagcaga caagcccgtc agggcgcgtc agcgggtgtt ggcgggtgtc ggggcgcagc   2902
catgacccag tcacgtagcg atagcggagt gtatactggc ttaactatgc ggcatcagag   2962
cagattgtac tgagagtgca ccatatatgc ggtgtgaaat accgcacaga tgcgtaagga   3022
gaaaataccg catcaggcgc tcttccgctt cctcgctcac tgactcgctg cgctcggtcg   3082
ttcggctgcg gcgagcggta tcagctcact caaaggcggt aatacggtta ccacagaat   3142
caggggataa gcaggaaag aacatgtgag caaaaggcca gcaaaggcc aggaaccgta    3202
aaaaggccgc gttgctggcg ttttccata ggctccgccc cctgacgag catcacaaaa    3262
atcgacgctc aagtcagagg tggcgaaacc cgacaggact ataaagatac caggcgtttc    3322
cccctggaag ctccctcgtg cgctctcctg ttccgaccct gccgcttacc ggatacctgt    3382
ccgcctttct cccttcggga agcgtggcgc tttctcatag ctcacgctgt aggtatctca    3442
gttcggtgta ggtcgttcgc tccaagctgg gctgtgtgca cgaacccccc gttcagcccg    3502
accgctgcgc cttatccggt aactatcgtc ttgagtccaa cccggtaaga cacgactat    3562
cgccactggc agcagccact ggtaacagga ttagcagagc gaggtatgta ggcggtgcta    3622
cagagttctt gaagtggtgg cctaactacg gctacactag aaggacagta tttggtatct    3682
gcgctctgct gaagccagtt accttcggaa aaagagttgg tagctcttga tccggcaaac    3742
aaaccaccgc tggtagcggt ggttttttg tttgcaagca gcagattacg cgcagaaaaa    3802
aaggatctca agaagatcct ttgatctttt ctacgggtc tgacgctcag tggaacgaaa    3862
actcacgtta agggatttg gtcatgaaca ataaaactgt ctgcttacat aaacagtaat    3922
acaaggggtg tt atg agc cat att caa cgg gaa acg tct tgc tct agg ccg    3973
              Met Ser His Ile Gln Arg Glu Thr Ser Cys Ser Arg Pro
```

-continued

```
                           365                       370
cga tta aat tcc aac atg gat gct gat tta tat ggg tat aaa tgg gct      4021
Arg Leu Asn Ser Asn Met Asp Ala Asp Leu Tyr Gly Tyr Lys Trp Ala
    375                 380                 385 cgc gat aat gtc ggg caa tca ggt gcg aca atc tat cga ttg tat ggg      4069
Arg Asp Asn Val Gly Gln Ser Gly Ala Thr Ile Tyr Arg Leu Tyr Gly
390                 395                 400                 405 aag ccc gat gcg cca gag ttg ttt ctg aaa cat ggc aaa ggt agc gtt      4117
Lys Pro Asp Ala Pro Glu Leu Phe Leu Lys His Gly Lys Gly Ser Val
                410                 415                 420 gcc aat gat gtt aca gat gag atg gtc aga cta aac tgg ctg acg gaa      4165
Ala Asn Asp Val Thr Asp Glu Met Val Arg Leu Asn Trp Leu Thr Glu
            425                 430                 435 ttt atg cct ctt ccg acc atc aag cat ttt atc cgt act cct gat gat      4213
Phe Met Pro Leu Pro Thr Ile Lys His Phe Ile Arg Thr Pro Asp Asp
        440                 445                 450 gca tgg tta ctc acc act gcg atc ccc ggg aaa aca gca ttc cag gta      4261
Ala Trp Leu Leu Thr Thr Ala Ile Pro Gly Lys Thr Ala Phe Gln Val
    455                 460                 465 tta gaa gaa tat cct gat tca ggt gaa aat att gtt gat gcg ctg gca      4309
Leu Glu Glu Tyr Pro Asp Ser Gly Glu Asn Ile Val Asp Ala Leu Ala
470                 475                 480                 485 gtg ttc ctg cgc cgg ttg cat tcg att cct gtt tgt aat tgt cct ttt      4357
Val Phe Leu Arg Arg Leu His Ser Ile Pro Val Cys Asn Cys Pro Phe
                490                 495                 500 aac agc gat cgc gta ttt cgt ctc gct cag gcg caa tca cga atg aat      4405
Asn Ser Asp Arg Val Phe Arg Leu Ala Gln Ala Gln Ser Arg Met Asn
            505                 510                 515 aac ggt ttg gtt gat gcg agt gat ttt gat gac gag cgt aat ggc tgg      4453
Asn Gly Leu Val Asp Ala Ser Asp Phe Asp Asp Glu Arg Asn Gly Trp
        520                 525                 530 cct gtt gaa caa gtc tgg aaa gaa atg cat aaa ctt ttg cca ttc tca      4501
Pro Val Glu Gln Val Trp Lys Glu Met His Lys Leu Leu Pro Phe Ser
    535                 540                 545 ccg gat tca gtc gtc act cat ggt gat ttc tca ctt gat aac ctt att      4549
Pro Asp Ser Val Val Thr His Gly Asp Phe Ser Leu Asp Asn Leu Ile
550                 555                 560                 565 ttt gac gag ggg aaa tta ata ggt tgt att gat gtt gga cga gtc gga      4597
Phe Asp Glu Gly Lys Leu Ile Gly Cys Ile Asp Val Gly Arg Val Gly
                570                 575                 580 atc gca gac cga tac cag gat ctt gcc atc cta tgg aac tgc ctc ggt      4645
Ile Ala Asp Arg Tyr Gln Asp Leu Ala Ile Leu Trp Asn Cys Leu Gly
            585                 590                 595 gag ttt tct cct tca tta cag aaa cgg ctt ttt caa aaa tat ggt att      4693
Glu Phe Ser Pro Ser Leu Gln Lys Arg Leu Phe Gln Lys Tyr Gly Ile
        600                 605                 610 gat aat cct gat atg aat aaa ttg cag ttt cat ttg atg ctc gat gag      4741
Asp Asn Pro Asp Met Asn Lys Leu Gln Phe His Leu Met Leu Asp Glu
    615                 620                 625 ttt ttc taagaattaa ttcatgagcg gatacatatt tgaatgtatt tagaaaaata      4797
Phe Phe
630 aacaaatagg ggttccgcgc acatttcccc gaaaagtgcc acctgaaatt gtaaacgtta      4857 atattttgtt aaaattcgcg ttaaattttt gttaaatcag ctcatttttt aaccaatagg      4917 ccgaaatcgg caaaatccct tataaatcaa agaatagacc gagatagggt tgagtgttg      4977 ttccagtttg gaacaagagt ccactattaa agaacgtgga ctccaacgtc aaagggcgaa      5037 aaaccgtcta tcagggcgat ggcccactac gtgaaccatc accctaatca agttttttgg      5097
```

-continued

```
ggtcgaggtg ccgtaaagca ctaaatcgga accctaaagg gagcccccga tttagagctt      5157
gacggggaaa gccggcgaac gtggcgagaa aggaagggaa gaaagcgaaa ggagcgggcg      5217
ctagggcgct ggcaagtgta gcggtcacgc tgcgcgtaac caccacaccc gccgcgctta      5277
atgcgccgct acagggcgcg tcccattcgc ca                                    5309
```

```
<210> SEQ ID NO 15
<211> LENGTH: 30
<212> TYPE: DNA
<213> ORGANISM: Artificial Sequence
<220> FEATURE:
<223> OTHER INFORMATION: primer, HT-YscF Start

<400> SEQUENCE: 15
ccggatccga tgagtaactt ctctggattt                                          30

<210> SEQ ID NO 16
<211> LENGTH: 30
<212> TYPE: DNA
<213> ORGANISM: Artificial Sequence
<220> FEATURE:
<223> OTHER INFORMATION: primer, HT-YscF Stop

<400> SEQUENCE: 16
ccgctcgagt gggaacttct gtaggatgcc                                          30

<210> SEQ ID NO 17
<211> LENGTH: 87
<212> TYPE: PRT
<213> ORGANISM: Yersinia pestis KIM5
<220> FEATURE:
<223> OTHER INFORMATION: YscF amino acid seuquence from Y. pestis KIM5
<220> FEATURE:
<223> OTHER INFORMATION: sequence can be found at MedLine accession
      number NC_004839

<400> SEQUENCE: 17

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 18
<211> LENGTH: 87
<212> TYPE: PRT
<213> ORGANISM: Yersinia pestis CO92
<220> FEATURE:
<223> OTHER INFORMATION: YscF amino acid sequence from Y. pestis CO92
<220> FEATURE:
<223> OTHER INFORMATION: sequence can be found at MedLine accession
      number NC_003131

<400> SEQUENCE: 18

Met Ser Asn Phe Ser Gly Phe Thr Lys Gly Thr Asp Ile Ala Asp Leu
1               5                   10                  15
```

```
Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 19
<211> LENGTH: 87
<212> TYPE: PRT
<213> ORGANISM: Artificial Sequence
<220> FEATURE:
<223> OTHER INFORMATION: Consensus sequence for YscF

<400> SEQUENCE: 19

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85

<210> SEQ ID NO 20
<211> LENGTH: 4884
<212> TYPE: DNA
<213> ORGANISM: Artificial Sequence
<220> FEATURE:
<223> OTHER INFORMATION: pBAD18-YscF
<220> FEATURE:
<221> NAME/KEY: misc_feature
<222> LOCATION: (96)..(974)
<223> OTHER INFORMATION: araC
<220> FEATURE:
<221> NAME/KEY: misc_feature
<222> LOCATION: (1003)..(1020)
<223> OTHER INFORMATION: operator O2
<220> FEATURE:
<221> NAME/KEY: promoter
<222> LOCATION: (1125)..(1153)
<223> OTHER INFORMATION: Pc promoter
<220> FEATURE:
<221> NAME/KEY: misc_feature
<222> LOCATION: (1161)..(1182)
<223> OTHER INFORMATION: operator O1
<220> FEATURE:
<221> NAME/KEY: misc_feature
<222> LOCATION: (1204)..(1217)
<223> OTHER INFORMATION: CAP site
<220> FEATURE:
<221> NAME/KEY: misc_feature
<222> LOCATION: (1213)..(1251)
<223> OTHER INFORMATION: operator I2 + I1
<220> FEATURE:
<221> NAME/KEY: promoter
<222> LOCATION: (1250)..(1277)
<223> OTHER INFORMATION: PBAD promoter
```

```
<220> FEATURE:
<221> NAME/KEY: CDS
<222> LOCATION: (1323)..(1586)
<223> OTHER INFORMATION: YscF
<220> FEATURE:
<221> NAME/KEY: misc_feature
<222> LOCATION: (1634)..(2059)
<223> OTHER INFORMATION: rrnB
<220> FEATURE:
<221> NAME/KEY: terminator
<222> LOCATION: (1634)..(2059)
<223> OTHER INFORMATION: rrnB
<220> FEATURE:
<221> NAME/KEY: promoter
<222> LOCATION: (2114)..(2120)
<223> OTHER INFORMATION: bla P3 promoter
<220> FEATURE:
<221> NAME/KEY: misc_feature
<222> LOCATION: (2152)..(3015)
<223> OTHER INFORMATION: bla
<220> FEATURE:
<221> NAME/KEY: rep_origin
<222> LOCATION: (3051)..(3509)
<223> OTHER INFORMATION: M13 origin
<220> FEATURE:
<221> NAME/KEY: rep_origin
<222> LOCATION: (3515)..(4212)
<223> OTHER INFORMATION: pBR322 origin

<400> SEQUENCE: 20
```

| | | |
|---|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcatttttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg caaatattg acggcagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaaatcga gataaccgtt ggcctcaatc | 900 |
| ggcgttaaac ccgccaccag atgggcatta acgagtatc ccggcagcag gggatcattt | 960 |
| tgcgcttcag ccatactttt catactcccg ccattcagag aagaaaccaa ttgtccatat | 1020 |
| tgcatcagac attgccgtca ctgcgtcttt tactggctct ctcgctaac caaaccggta | 1080 |
| accccgctta ttaaaagcat tctgtaacaa agcgggacca aagccatgac aaaaacgcgt | 1140 |
| aacaaaagtg tctataatca cggcagaaaa gtccacattg attatttgca cggcgtcaca | 1200 |
| ctttgctatg ccatagcatt tttatccata agattagcgg atcctacctg acgcttttta | 1260 |
| tcgcaactct ctactgtttc tccatacccg ttttttggg ctagcgaatt caggaggaaa | 1320 |

```
cg atg agt aac ttc tct gga ttt acg aaa gga acc gat atc gca gac    1367
   Met Ser Asn Phe Ser Gly Phe Thr Lys Gly Thr Asp Ile Ala Asp
   1               5                  10                  15
```

-continued

| | |
|---|---|
| tta gat gcg gtg gct caa acg ctc aag aag cca gca gac gat gca aac<br>Leu Asp Ala Val Ala Gln Thr Leu Lys Lys Pro Ala Asp Asp Ala Asn<br>              20                        25                        30 | 1415 |
| aaa gcg gtt aat gac tcg ata gca gca ttg aaa gat aag cct gac aac<br>Lys Ala Val Asn Asp Ser Ile Ala Ala Leu Lys Asp Lys Pro Asp Asn<br>              35                        40                        45 | 1463 |
| ccg gcg cta ctt gct gac tta caa cat tca att aat aaa tgg tcg gta<br>Pro Ala Leu Leu Ala Asp Leu Gln His Ser Ile Asn Lys Trp Ser Val<br>        50                        55                        60 | 1511 |
| att tac aat ata aac tca acc ata gtt cgt agc atg aaa gac tta atg<br>Ile Tyr Asn Ile Asn Ser Thr Ile Val Arg Ser Met Lys Asp Leu Met<br>65                        70                        75 | 1559 |
| caa ggc atc cta cag aag ttc cca taa ggatcccgcg gggatcctct<br>Gln Gly Ile Leu Gln Lys Phe Pro<br>80                        85 | 1606 |
| agagtcgacc tgcaggcatg caagcttggc tgttttggcg atgagagaa gattttcagc | 1666 |
| ctgatacaga ttaaatcaga acgcagaagc ggtctgataa acagaatt gcctggcggc | 1726 |
| agtagcgcgg tggtcccacc tgaccccatg ccgaactcag aagtgaaacg ccgtagcgcc | 1786 |
| gatggtagtg tggggtctcc ccatgcgaga gtagggaact gccaggcatc aaataaaacg | 1846 |
| aaaggctcag tcgaaagact gggcctttcg ttttatctgt tgtttgtcgg tgaacgctct | 1906 |
| cctgagtagg acaaatccgc cgggagcgga tttgaacgtt gcgaagcaac ggcccggagg | 1966 |
| gtggcgggca ggacgcccgc cataaactgc caggcatcaa attaagcaga aggccatcct | 2026 |
| gacggatggc cttttttgcgt ttctacaaac tcttttgttt attttctaa atacattcaa | 2086 |
| atatgtatcc gctcatgaga caataaccct gataaatgct tcaataatat tgaaaagga | 2146 |
| agagtatgag tattcaacat ttccgtgtcg cccttattcc cttttttgcg gcattttgcc | 2206 |
| ttcctgtttt tgctcaccca gaaacgctgg tgaaagtaaa agatgctgaa gatcagttgg | 2266 |
| gtgcacgagt gggttacatc gaactggatc tcaacagcgg taagatcctt gagagttttc | 2326 |
| gccccgaaga acgttttcca atgatgagca cttttaaagt tctgctatgt ggcgcggtat | 2386 |
| tatcccgtgt tgacgccggg caagagcaac tcggtcgccg catacactat tctcagaatg | 2446 |
| acttggttga gtactcacca gtcacagaaa agcatcttac ggatggcatg acagtaagag | 2506 |
| aattatgcag tgctgccata accatgagtg ataacactgc ggccaactta cttctgacaa | 2566 |
| cgatcggagg accgaaggag ctaaccgctt ttttgcacaa catgggggat catgtaactc | 2626 |
| gccttgatcg ttgggaaccg gagctgaatg aagccatacc aaacgacgag cgtgacacca | 2686 |
| cgatgcctgc agcaatggca acaacgttgc gcaaactatt aactggcgaa ctacttactc | 2746 |
| tagcttcccg gcaacaatta atagactgga tggaggcgga taaagttgca ggaccacttc | 2806 |
| tgcgctcggc ccttccggct ggctggttta ttgctgataa atctggagcc ggtgagcgtg | 2866 |
| ggtctcgcgg tatcattgca gcactggggc cagatggtaa gccctcccgt atcgtagtta | 2926 |
| tctacacgac ggggagtcag gcaactatgg atgaacgaaa tagacagatc gctgagatag | 2986 |
| gtgcctcact gattaagcat tggtaactgt cagaccaagt ttactcatat atactttaga | 3046 |
| ttgatttacg cgcccgtag cggcgcatta agcgcggcgg gtgtggtggt tacgcgcagc | 3106 |
| gtgaccgcta cacttgccag cgccctagcg cccgctcctt tcgctttctt cccttccttt | 3166 |
| ctcgccacgt tcgccggctt tccccgtcaa gctctaaatc gggggctccc tttagggttc | 3226 |
| cgatttagtg ctttacggca cctcgacccc aaaaaacttg atttgggtga tggttcacgt | 3286 |
| agtgggccat cgccctgata gacggttttt cgccctttga cgttggagtc acgttcttt | 3346 |
| aatagtggac tcttgttcca aacttgaaca acactcaacc ctatctcggg ctattctttt | 3406 |

-continued

```
gatttataag ggattttgcc gatttcggcc tattggttaa aaaatgagct gatttaacaa      3466
aaatttaacg cgaattttaa caaaatatta acgtttacaa tttaaaagga tctaggtgaa      3526
gatcctttt gataatctca tgaccaaaat cccttaacgt gagttttcgt tccactgagc       3586
gtcagacccc gtagaaaaga tcaaaggatc ttcttgagat cctttttttc tgcgcgtaat      3646
ctgctgcttg caaacaaaaa aaccaccgct accagcggtg gtttgtttgc cggatcaaga      3706
gctaccaact cttttccga aggtaactgg cttcagcaga gcgcagatac caaatactgt      3766
ccttctagtg tagccgtagt taggccacca cttcaagaac tctgtagcac cgcctacata     3826
cctcgctctg ctaatcctgt taccagtggc tgctgccagt ggcgataagt cgtgtcttac      3886
cgggttggac tcaagacgat agttaccgga taaggcgcag cggtcgggct gaacgggggg      3946
ttcgtgcaca cagcccagct tggagcgaac gacctacacc gaactgagat acctacagcg      4006
tgagctatga gaaagcgcca cgcttcccga agggagaaag gcggacaggt atccggtaag      4066
cggcagggtc ggaacaggag agcgcacgag ggagcttcca gggggaaacg cctggtatct      4126
ttatagtcct gtcgggtttc gccacctctg acttgagcgt cgattttgt gatgctcgtc       4186
aggggggcgg agcctatgga aaaacgccag caacgcggcc ttttacggt tcctggcctt       4246
ttgctggcct tttgctcaca tgttctttcc tgcgttatcc cctgattctg tggataaccg      4306
tattaccgcc tttgagtgag ctgataccgc tcgccgcagc cgaacgaccg agcgcagcga      4366
gtcagtgagc gaggaagcgg aagagcgcct gatgcggtat tttctcctta cgcatctgtg      4426
cggtatttca caccgcatat ggtgcactct cagtacaatc tgctctgatg ccgcatagtt      4486
aagccagtat acactccgct atcgctacgt gactgggtca tggctgcgcc ccgacacccg      4546
ccaacacccg ctgacgcgcc ctgacgggct tgtctgctcc cggcatccgc ttacagacaa      4606
gctgtgaccg tctccgggag ctgcatgtgt cagaggtttt caccgtcatc accgaaacgc      4666
gcgaggcagc aaggagatgg cgcccaacag tcccccggcc acggggcctg ccaccatacc     4726
cacgccgaaa caagcgctca tgagcccgaa gtggcgagcc cgatcttccc catcggtgat      4786
gtcggcgata taggcgccag caaccgcacc tgtggcgccg gtgatgccgg ccacgatgcg      4846
tccggcgtag aggatctgct catgtttgac agcttatc                              4884
```

What is claimed is:

1. A composition produced by a process, the process comprising:
   providing a host cell with an expression vector including a nucleotide sequence encoding a His-tagged YscF protein comprising SEQ ID NO: 12;
   expressing the nucleotide sequence in the host cell to produce the His-tagged YscF protein;

collecting the His-tagged YscF protein; and mixing the collected His-tagged YscF protein with a suitable excipient so as to form the composition.

2. The composition produced by the process of claim 1, further comprising mixing LcrV, the F1 antigen, YopD or combinations thereof with the suitable excipient.

3. The composition produced by the process of claim 1, further comprising mixing an adjuvant with the suitable excipient.

4. The composition produced by the process of claim 1, further comprising mixing PrgI, MxiH, EscF or combinations thereof with the suitable excipient.

5. An isolated or recombinant YscF protein capable of providing protection to an animal against a pathogen of *Yersinia* origin, wherein the isolated or recombinant YscF protein is encoded by a nucleotide sequence selected from the group of nucleotide sequences consisting of SEQ ID NO: 11 and SEQ ID NO: 13.

6. A His-tagged YscF protein, wherein the peptide sequence is SEQ ID NO: 12.

* * * * *

UNITED STATES PATENT AND TRADEMARK OFFICE
CERTIFICATE OF CORRECTION

PATENT NO. : 7,344,718 B2  
APPLICATION NO. : 10/622220  
DATED : March 18, 2008  
INVENTOR(S) : Matthew L. Nilles and Jyl S. Matson Page 1 of 1

It is certified that error appears in the above-identified patent and that said Letters Patent is hereby corrected as shown below:

On the title page:
In ITEM (57) ABSTRACT, line 12,   Change "or a" to --of a--

In the specification:
COLUMN 13, LINE 52,   Change "Nines," to --Nilles,--
COLUMN 37, SEQUENCE 15,   Change "ccggatccga" to --cgggatccga-- so that sequence 15 reads as follows:

```
<210>   SEQ ID NO 15
<211>   LENGTH:   30
<212>   TYPE:  DNA
<213>   ORGANISM:   Artificial Sequence
<220>   FEATURE:
<223>   OTHER INFORMATION:   primer, HT-YscF Start

<400>   SEQUENCE:   15 cgggatccga tgagtaactt ctctggattt                         30
```

Signed and Sealed this
Twelfth Day of March, 2013

Teresa Stanek Rea
*Acting Director of the United States Patent and Trademark Office*